(12) United States Patent
Forster

(10) Patent No.: US 7,224,273 B2
(45) Date of Patent: May 29, 2007

(54) DEVICE AND METHOD FOR IDENTIFYING A CONTAINER

(76) Inventor: Ian J. Forster, 31 Great Cob, Chelmsford, Essex (GB) CM1 6LA ( * ) Notice: Subject to any disclaimer, the term of this patent is extended or adjusted under 35 U.S.C. 154(b) by 454 days.

(21) Appl. No.: 10/422,634

(22) Filed: Apr. 24, 2003

(65) Prior Publication Data

US 2004/0041709 A1    Mar. 4, 2004

Related U.S. Application Data

(60) Provisional application No. 60/382,883, filed on May 23, 2002.

(51) Int. Cl.
*G08B 1/08*    (2006.01)
(52) U.S. Cl. .............................. 340/539.1; 340/539.29; 340/572.1; 340/571
(58) Field of Classification Search ............ 340/539.1, 340/539.29, 603, 612, 572.1, 571
See application file for complete search history.

(56) References Cited

U.S. PATENT DOCUMENTS

| | | | |
|---|---|---|---|
| 3,779,418 A | 12/1973 | Davis | 220/60 |
| 3,787,993 A | 1/1974 | Lyon | 40/306 |
| 3,817,417 A | 6/1974 | Edwards | 217/37 |
| 3,930,593 A | 1/1976 | Ragettli | 220/276 |
| 3,934,749 A | 1/1976 | Andrulionis | 220/63 R |
| 3,961,323 A | 6/1976 | Hartkorn | 340/280 |
| 4,343,325 A | 8/1982 | Fallon | 137/212 |
| 4,384,289 A | 5/1983 | Stillwell et al. | 340/870.17 |
| 4,630,044 A | 12/1986 | Polzer | 340/825.72 |
| 4,736,926 A | 4/1988 | Fallon et al. | 251/149.9 |
| 4,744,162 A | 5/1988 | Okazaki | 40/312 |
| 4,862,160 A | 8/1989 | Ekchian et al. | 340/825.54 |
| 4,944,363 A | 7/1990 | Osher et al. | 273/58 A |
| 4,975,711 A | 12/1990 | Lee | 343/702 |
| 5,021,767 A | 6/1991 | Fockens | 340/572 |
| 5,057,844 A | 10/1991 | Rothstein | 342/51 |

(Continued)

FOREIGN PATENT DOCUMENTS

DE    44 46 203 A1    6/1996

(Continued)

*Primary Examiner*—Daryl C Pope
(74) *Attorney, Agent, or Firm*—Christensen O'Connor Johnson Kindness PLLC

(57) ABSTRACT

The present invention relates to an wireless communication device and method for identifying a container. The device includes a wireless communication device for transmitting information regarding the container. The container includes an outer wall forming an enclosed interior chamber for containing contents, such as solid, liquid, and/or gaseous materials. The container also includes an opening through which the container contents are distributed. A valve assembly is positioned over the opening for controlling the flow of contents from the container. The wireless communication device is mounted within the valve assembly, and preferably within the ball. The wireless communication device communicates information regarding the container and/or its contents to an interrogation reader. The temperature associated with the container and/or its contents may be determined by various techniques including thermal contact between the temperature sensor and the container, measuring the discharge rate in a discharge capacitor associated with the wireless communication device, and determining the maximum energy absorption frequency of the wireless communication device to correlate it to temperature. The liquid level of the container may be determined by employing liquid level sensor techniques.

88 Claims, 14 Drawing Sheets

U.S. PATENT DOCUMENTS

| | | | |
|---|---|---|---|
| 5,151,684 A | 9/1992 | Johnsen | 340/572 |
| 5,161,892 A | 11/1992 | Shigezawa et al. | 374/179 |
| 5,190,504 A | 3/1993 | Scatterday | 482/49 |
| 5,326,939 A | 7/1994 | Schafer | 177/139 |
| 5,396,218 A | 3/1995 | Olah | 340/572 |
| 5,448,220 A | 9/1995 | Levy | 340/539 |
| 5,491,483 A | 2/1996 | D'hont | 342/42 |
| 5,524,750 A | 6/1996 | Miller | 206/767 |
| 5,564,166 A | 10/1996 | Roy | 24/3.11 |
| 5,585,953 A | 12/1996 | Zavrel | 359/152 |
| 5,603,430 A * | 2/1997 | Loehrke et al. | 222/1 |
| 5,609,406 A | 3/1997 | Cejnek | 362/61 |
| 5,619,207 A | 4/1997 | D'Hont | 342/42 |
| 5,621,913 A | 4/1997 | Tuttle et al. | 455/90 |
| 5,631,631 A | 5/1997 | Deschenes | 340/572 |
| 5,648,765 A | 7/1997 | Cresap et al. | 340/825.35 |
| 5,663,630 A | 9/1997 | Koziatek | 320/49 |
| 5,696,485 A | 12/1997 | Treharne | 340/505 |
| 5,743,134 A | 4/1998 | Dreyer | |
| 5,767,772 A | 6/1998 | Lemaire | 340/571 |
| 5,767,792 A | 6/1998 | Urbas et al. | 340/870.17 |
| 5,779,839 A | 7/1998 | Tuttle et al. | 156/213 |
| 5,781,112 A | 7/1998 | Shymko | 340/572 |
| 5,790,029 A | 8/1998 | Curnutte et al. | 340/572 |
| 5,798,693 A | 8/1998 | Engellenner | 340/505 |
| 5,831,531 A | 11/1998 | Tuttle | 340/572 |
| 5,833,603 A | 11/1998 | Kovacs et al. | 600/317 |
| 5,842,118 A | 11/1998 | Wood, Jr. | 455/101 |
| 5,864,580 A | 1/1999 | Lowe et al. | 375/222 |
| 5,865,339 A | 2/1999 | Carlson | 220/694 |
| 5,883,376 A | 3/1999 | Rosch et al. | 235/492 |
| 5,887,176 A | 3/1999 | Griffith et al. | 395/750 |
| 5,905,444 A | 5/1999 | Zimmer | 340/825.31 |
| 5,926,013 A | 7/1999 | Brandt | 323/370 |
| 5,936,523 A | 8/1999 | West | 340/545.6 |
| 5,939,977 A | 8/1999 | Monson | 340/442 |
| 5,947,256 A | 9/1999 | Patterson | 194/209 |
| 5,953,682 A | 9/1999 | McCarrick et al. | 702/45 |
| 5,959,524 A | 9/1999 | Wienand et al. | 338/28 |
| 5,961,215 A | 10/1999 | Lee et al. | 374/178 |
| 5,963,177 A | 10/1999 | Tuttle et al. | 343/872 |
| 5,972,156 A | 10/1999 | Brady et al. | 156/280 |
| 5,973,611 A | 10/1999 | Kulha et al. | 340/825.31 |
| 5,986,569 A | 11/1999 | Mish et al. | 340/825.54 |
| 6,008,727 A | 12/1999 | Want et al. | 340/572.1 |
| 6,012,415 A | 1/2000 | Linseth | 119/174 |
| 6,023,244 A | 2/2000 | Snygg et al. | 343/700 MS |
| 6,031,459 A | 2/2000 | Lake | 340/572.8 |
| 6,069,564 A | 5/2000 | Hatano et al. | 340/572.7 |
| 6,078,259 A | 6/2000 | Brady et al. | 340/572.7 |
| 6,138,058 A | 10/2000 | Van Antwerp, Jr. et al. | 700/225 |
| 6,147,604 A | 11/2000 | Wiklof et al. | 340/572.1 |
| 6,204,764 B1 | 3/2001 | Maloney | 340/588.1 |
| 6,206,282 B1 | 3/2001 | Hayes, Sr. et al. | 235/375 |
| 6,402,690 B1 | 6/2002 | Rhee et al. | 600/300 |
| 6,469,627 B1 | 10/2002 | Forster et al. | 340/572.8 |
| 6,483,473 B1 | 11/2002 | King et al. | 343/767 |
| 6,501,435 B1 | 12/2002 | King et al. | 343/795 |
| 2002/0047781 A1 | 4/2002 | Fallah | |

FOREIGN PATENT DOCUMENTS

| | | |
|---|---|---|
| DE | 295 04 712 U | 7/1996 |
| DE | 197 03 819 C1 | 8/1998 |
| EP | 0 467 657 A1 | 1/1992 |
| FR | 2681972 A | 4/1993 |
| GB | 974 249 A | 11/1964 |
| GB | 2 092 096 A | 8/1982 |
| GB | 2 210 349 A | 6/1989 |
| GB | 2 293 588 A | 4/1996 |
| GB | 2346604 | 8/2000 |
| WO | WO 94/05090 | 3/1994 |
| WO | 94/27117 A1 | 11/1994 |
| WO | WO 95/15622 | 6/1995 |
| WO | WO 99/18000 | 4/1999 |
| WO | 01/59699 A2 | 8/2001 |

* cited by examiner

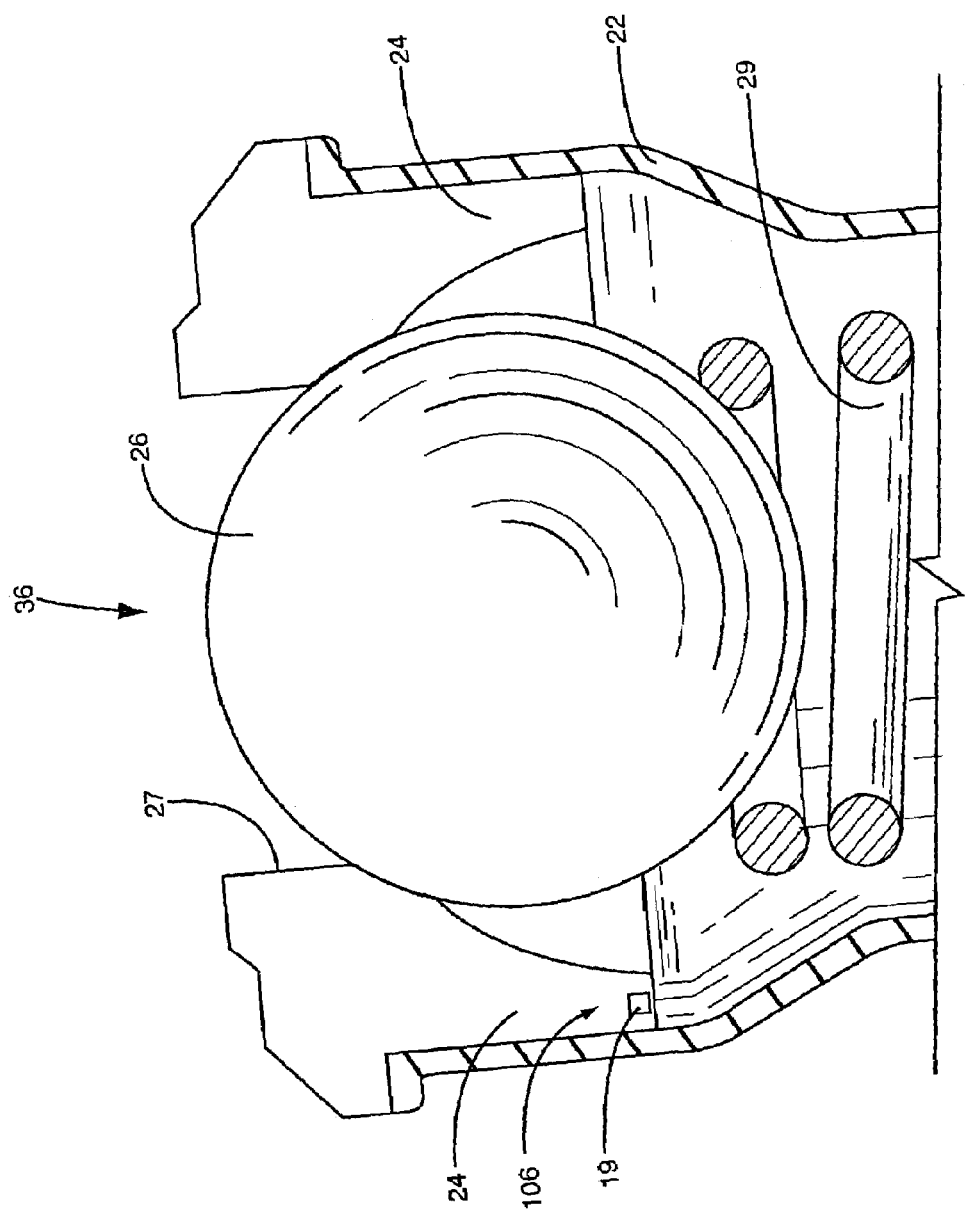

DEVICE AND METHOD FOR IDENTIFYING A CONTAINER

RELATED APPLICATION

This application claims priority and the benefit of U.S. Provisional Patent Application Ser. No. 60/382,883 filed May 23, 2002, which is incorporated by reference herein in its entirety.

FIELD OF THE INVENTION

The present invention relates generally to a device and method for identifying a container and, more particularly, to a radio frequency wireless communication device and a method for placing such a device inside a container.

BACKGROUND OF THE INVENTION

It is often necessary to monitor the location and movement of materials within a distribution center or manufacturing facility. One method of tracking the materials is to attach a wireless communication device, such as a radio frequency identification (RFID) transponder or other wireless communication device, to containers that are housing the materials. By way of example, a liquid container, such as a barrel or keg, may include a wireless communication device indicative of the liquid contained inside. A transmission device, such as an interrogation reader or transmitter, having an antenna device, is able to send information wirelessly through electronic signals. Such transmission device is placed throughout the distribution or manufacturing facility to receive signals transmitted from wireless communication devices. The signals are then passed to a central control system that monitors and records the applicable information. The central control system can also send information to its interrogation readers to send to the transponders for response and/or to be stored in the transponder's memory.

The information communicated by the containers in the system to the interrogation readers may be used for a number of reasons. For example, a statistical analysis may be made of the materials to maintain accurate inventories, production flow rates, and other production standards. Additionally, the wireless communication devices may include specific information about the materials housed within the containers, including, but not limited to, date of manufacture, place of manufacture, type of product within the container, "born on" date, temperature of the container and ambient air, temperature of the contents of the container, and pressure of the container.

The wireless communication device includes an antenna arrangement to communicate information about the containers to the interrogation readers. It is generally known for wireless communication devices to include an antenna. It is often a problem for many wireless communication devices to provide an effective antenna arrangement, especially if the wireless communication device is small or is required to be placed in a contained area. The length of the antenna must be tailored to the specific frequency at which the wireless communication device is designed to operate. For low frequencies in the MHz range or lower, an antenna may have to be several inches long to several feet long. The antenna may have to be several inches long for higher frequencies, to allow successful communication at the desired operating frequency.

Additionally, the antenna must either be packaged inside the wireless communication packaging that houses the wireless communication device, or located external to the wireless communication device. External positioning of the antenna to the wireless communication device provides several other challenges when placing the wireless communication device in a confined area, such as in a container. The antenna may have additional problems radiating energy effectively if the antenna is contained internal to a device, such as a container.

Another problem occurs when a wireless communication device cannot be easily mounted to a container. One example of such a container is a beer keg. A beer keg has a substantially cylindrical shape with smooth, uniform outer walls. There are no extensions or areas for effectively attaching a wireless communication device on the outside of the container. Additionally, containers may be heavy and cumbersome to handle. During the filling and distribution process, containers may bang against other containers, storage racks, conveyor equipment, etc. A wireless communication device attached to an exterior portion of the container may easily be damaged or destroyed during this process.

A container, such as a beer keg, may include a valve assembly for dispensing the contents. In many containers, the valve assembly includes a neck extending from an upper container surface. A ball is positioned within the neck and is movable between an open orientation that permits the contents to exit the container and a closed orientation that prevents the exit of the contents. A gasket may be positioned around the ball to prevent the leaking of the liquid contents from the container when the ball is in the closed orientation. A tap is mounted on the neck and ball to bias the ball in the open position and add air pressure to force the contents from the container.

To address the problems described above, it is advantageous to use the valve assembly of a container to mount a wireless communication device.

SUMMARY OF THE INVENTION

The present invention includes a wireless communication device mounted within a valve assembly of a container. Placement of the wireless communication device within the valve assembly protects the wireless communication device from damage during handling of the container. Such placement also removes the wireless communication device from view of consumers, preventing removal of the device or other damage by consumers. Additionally, placement of the wireless communication device within the valve assembly may allow for sensors to be placed within the wireless communication device, or in communication with the wireless communication device, to obtain readings about the container contents and the container interior.

The wireless communication device provides wireless communication for identifying the container and/or its contents. The wireless communication device can communicate, and preferably also receive, transmissions to and from an outside source. The device may further include a control system and memory for storing data related to the container and/or its contents. In one embodiment, the wireless communication device is an integrated circuit with a pole antenna. In another embodiment, the wireless communication device uses a part of the valve assembly to form a slot antenna.

The container, according to the present invention, can be a variety of designs. One container embodiment includes an outer wall, top wall, and bottom wall forming an enclosed interior chamber for containing materials or other contents, and having an opening for dispensing the contents. In one embodiment, the container is a keg, for housing liquid, such as beer. The valve assembly is positioned over the opening to control the content flow. The wireless communication device is mounted within the valve assembly, such that the wireless communication device is protected from damage. The wireless communication device is also adapted to obtain measurements from the container interior.

The valve assembly may include a ball positioned over the opening of the container. The wireless communication device and its antenna may be mounted inside the ball. In one embodiment, the ball is constructed of a conductive material, such as stainless steel, which is commonly used in many valve assemblies. A conductive ball may be used, provided its material does not interfere with communication from and/or to the wireless communication device. If the conductive material obstructs communication, the ball may alternatively be constructed of a non-conductive material. In this embodiment, the ball is constructed out of a consumption-safe, non-conductive material if the container contains consumable materials.

The wireless communication device may also communicate the temperature of the container and/or its contents wirelessly. In an embodiment, the wireless communication device is associated with a temperature sensor that senses the temperature of the container and/or its contents. The wireless communication device is placed in thermal contact with the contents of the container. One manner of placing the wireless communication device in thermal contact with the contents of the container is to place the wireless communication device inside the ball of the valve assembly, if the ball is in thermal contact with the contents of the container.

In another temperature sensing embodiment, the wireless communication device may include a discharge capacitor. The discharge rate of the discharge capacitor during a given time can be used to determine the temperature of the container and/or its contents.

In another temperature sensing embodiment, an interrogation reader determines the temperature of the container and/or its contents by determining the temperature of the wireless communication device. The temperature of the wireless communication device correlates to the temperature associated with the container and/or its contents. A frequency at which the wireless communication device has maximum energy absorption is ascertained. This maximum energy absorption frequency can be correlated to the average temperature of the wireless communication device over a given journey.

Additionally, the invention may determine the level of the contents of the container. If the contents are liquid, a liquid level sensor may be placed in the fill tube to measure the variations in the liquid level. The level of the contents is communicated to the wireless communication device that in turn communicates such information wirelessly. One method of determining liquid level involves determining the resonance frequency of the container, and correlating the resonance frequency to liquid level in the container.

The invention also includes a method of monitoring a container and/or its contents. While the container is within a facility, such as during manufacturing, filling, or storing, the container is moved through at least one interrogation point containing an interrogation reader. Communication between the wireless communication device and the interrogation reader is established for monitoring the location and/or content information about the container. A central control system may be in communication with the interrogation point for monitoring the movement of the container. The central control system may monitor the position of the container, or it may also monitor specific information that is stored within memory in the wireless communication device.

BRIEF DESCRIPTION OF THE DRAWINGS

FIG. 6 is a schematic diagram of an antenna arrangement with the antenna internal to the transponder packaging;

DETAILED DESCRIPTION OF THE INVENTION

Figure 1:
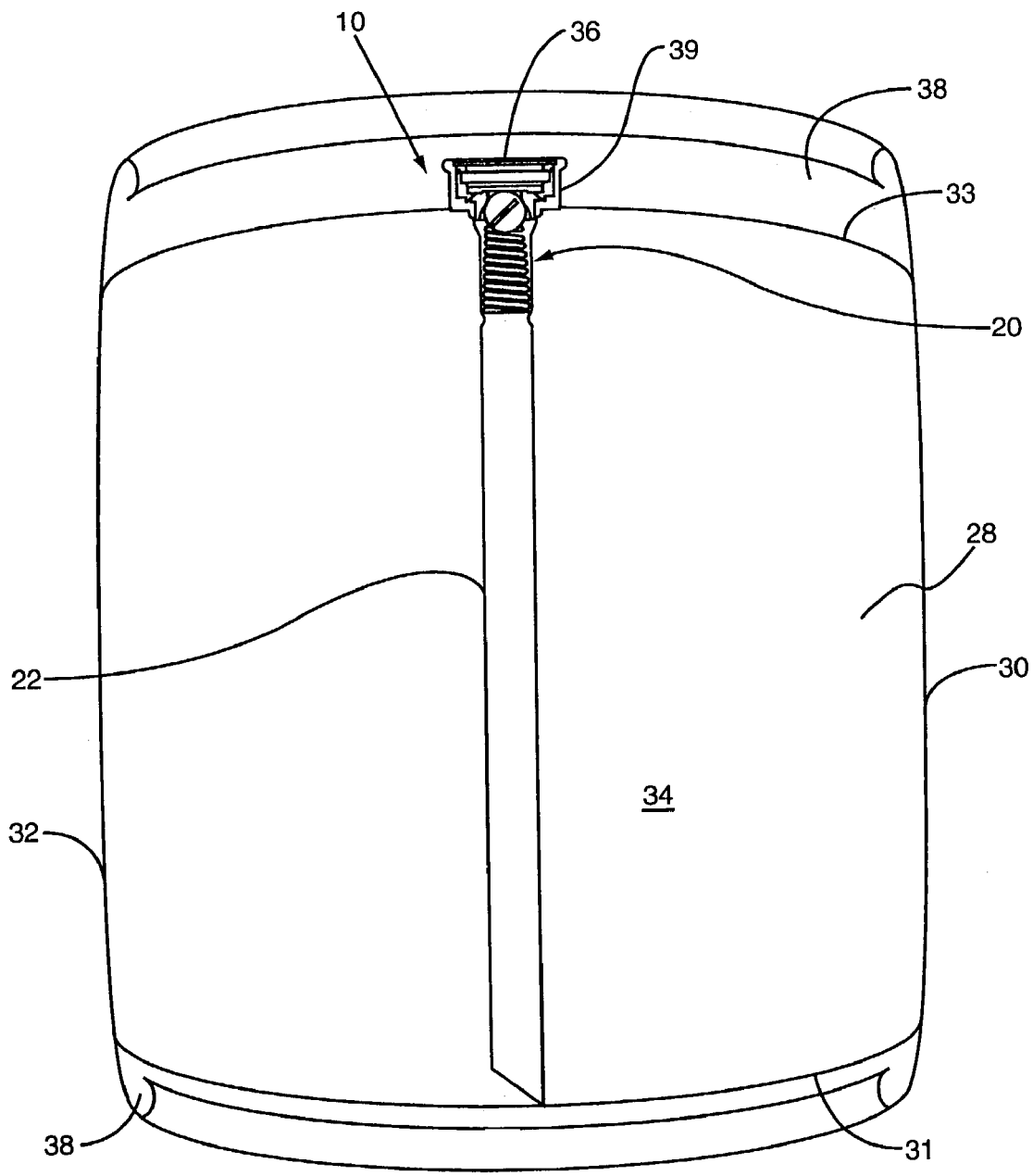
FIG. 1 is a cross sectional side view of a container with a valve assembly constructed in accordance with the present invention.

The present invention is directed to a device and method for identifying a container. The invention includes a wireless communication device 10 that is mounted in a valve assembly 20, within a container 30, for identifying the container 30. The valve assembly 20 is positioned within the container 30, and includes a ball 26, gasket 24, and biasing member 29. The wireless communication device 10 includes a transponder 19 for identifying and storing information regarding the container 30 and/or its contents 28. The contents 28 may be any type of solid, liquid, and/or gaseous material. An interrogation system monitors the individual containers 30 that are stored and/or moved throughout a facility, such as a manufacturing or distribution facility.

FIG. 1 illustrates one type of container 30 and valve assembly 20 applicable to the present invention. The container has outer walls including a bottom wall 31, top wall 33, and side walls 32 sealed together forming an enclosed interior chamber 34 for housing contents 28. In this particular embodiment, the container 30 is a keg for holding a liquid 28, such as beer. However, the container 30 may be used to house any type of contents. An opening 36, for dispensing the liquid 28, is situated along one of the outer walls, and preferably the top wall 33. A rim 38, formed by the side wall 32, may extend above and below the top and bottom walls, 33 and 31 respectively, for handling the container 30, and protecting the opening 36 and valve assembly 20.

Figure 2:
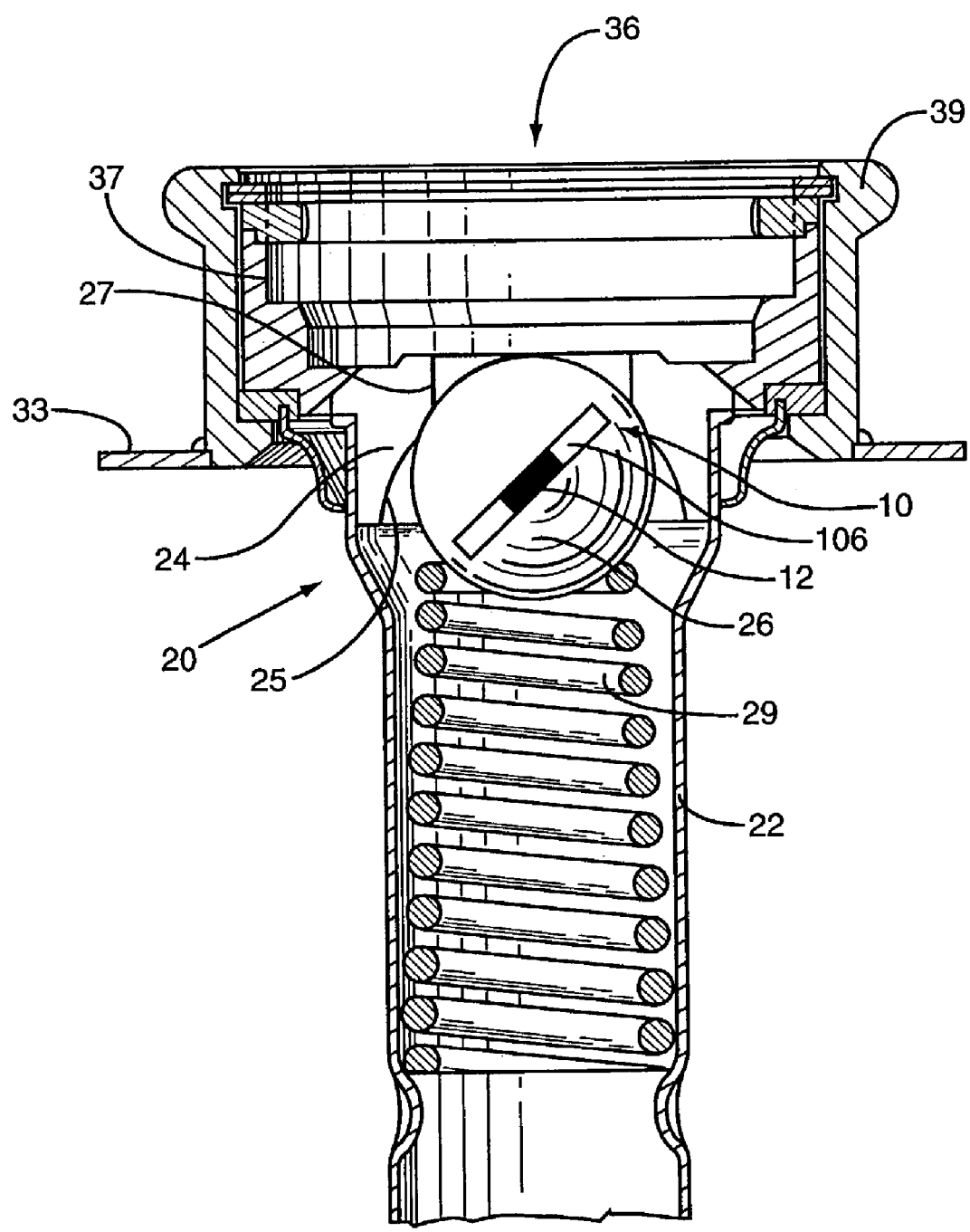
FIG. 2 is a partial cross sectional side view of the valve assembly, illustrating a gasket, biasing member, and ball with inserted wireless communication device.

A neck 39 extends from the top wall 33 around the opening 36. As illustrated in FIG. 2, the neck 39 may include fittings 37 for receiving a tap (not illustrated) when dispensing the liquid 28. A fill tube 22 is aligned with the opening 36 and extends between the top wall 33 to a lower area of the interior chamber 34 in proximity to the bottom wall 31. The fill tube 22 is hollow, and has openings on each end allowing the liquid 28 to enter and exit. As pressure is introduced into the chamber 34, the liquid 28 is forced through the fill tube 22 and out through the opening 36.

The valve assembly 20 is disposed within the opening 36, as best illustrated in FIG. 2. The ball 26 is positioned within the fill tube 22 and opening 36 for controlling the flow of the liquid 28 from the container 30. The ball 26 is preferably spherical, and is positioned within a mounting structure 24 for maintaining the proper positioning within the fill tube 22 and opening 36. A gasket 24 is positioned around the circumference of the opening 36 and is contacted by the ball 26 to prevent fluid 28 from escaping from the container 30. In one embodiment, the gasket 24 is substantially funnel-shaped having angled outer edges 25 that narrow into seated edges 27 aligned with the center of the fill tube 22 and opening 36.

A biasing member 29 is positioned adjacent the ball 26 for forcing the ball 26 against the gasket 24. The biasing member 29 has a helical orientation providing a supporting surface for containing the ball 26 as illustrated in FIG. 2. In one embodiment, the ball 26 is spherical and may rotate and change orientation relative to the container 30 during use. In an open orientation, the ball 26 is biased downward against the biasing member 29, forming openings between the ball 26 and gasket 24. This allows the liquid 28 to exit. In a closed orientation, as illustrated in FIG. 2, the ball 26 is biased upward against the gasket 24, forming a liquid-tight seal. U.S. Pat. No. 4,343,325, entitled "Valve assembly and coupler therefor," and U.S. Pat. No. 4,736,926, entitled "Valve assembly and coupler therefor," disclose designs for containers and valve assemblies, both of which are incorporated herein by reference in their entirety.

Figure 3:
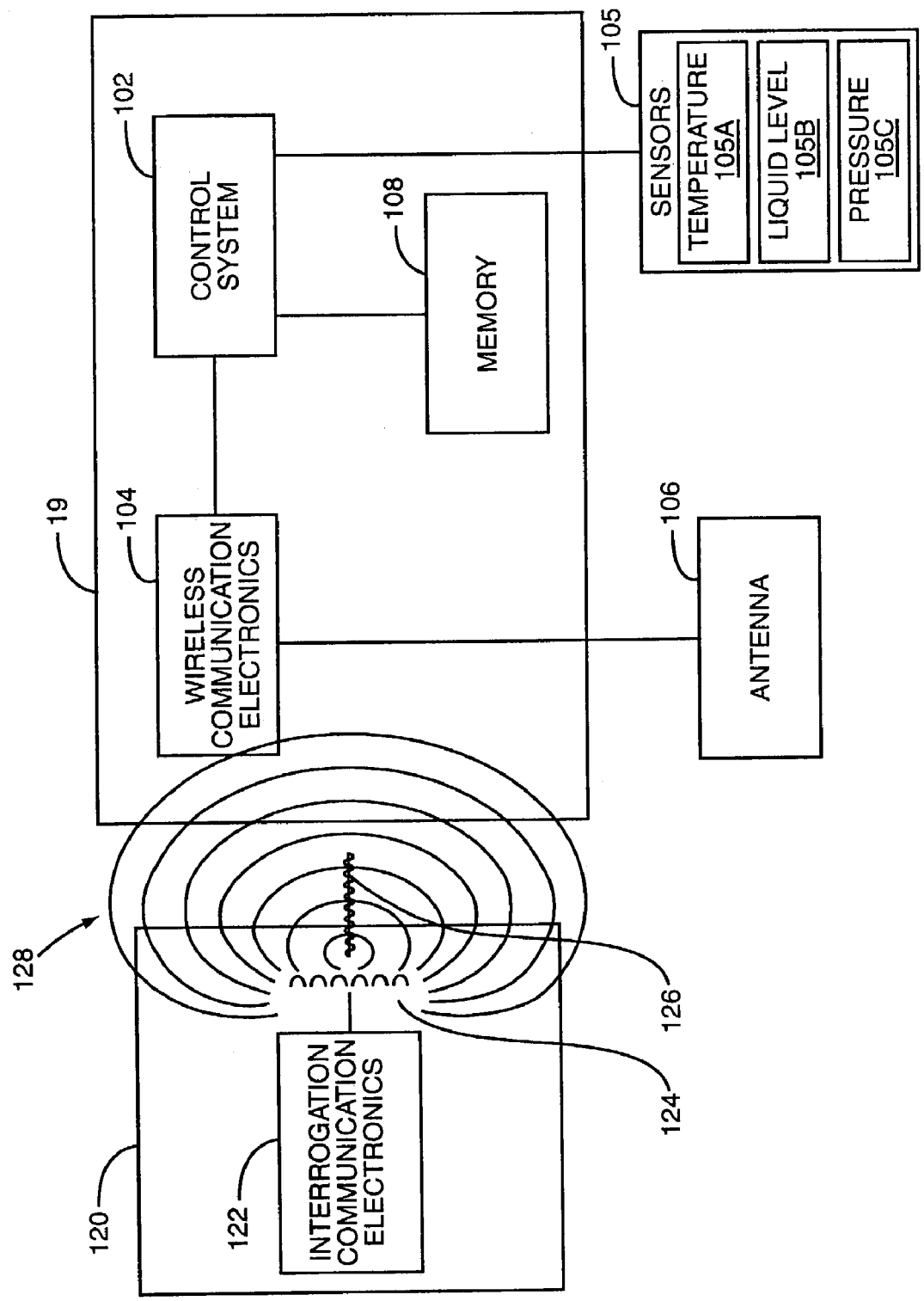
FIG. 3 is a schematic diagram illustrating communication between the wireless communication device and an interrogation reader.

FIG. 3 illustrates one particular type of wireless communication device 10 called a radio frequency transponder 19. One of ordinary skill in the art will understand that there are many other different types of wireless communication devices that allow electronic communication, and the present invention is not limited to any one particular type.

The transponder 19 is usually made out of some type of plastic packaging, epoxy, or other material having within it a control system 102, wireless communication electronics 104, and memory 108. An antenna 106 provides communication to and from the transponder 19. The antenna 106 may be either external to or incorporated internally within the transponder 19 packaging. The terms "transponder" 19 and "wireless communication device" 19 are used interchangeably herein, and the present invention is not limited to use of a transponder. The present invention is applicable to all types of wireless communication devices 19, including transponders 19.

The control system 102 is an integrated circuit, or other type of microprocessor or micro-controller electronics, that controls the substantive operations of the transponder 19. The control system 102 is connected to the wireless communication electronics 104 to communicate and receive transmissions. The control system 102 is also connected to memory 108 for storing and retrieving information, such as identification information, or other information, concerning the container and/or its contents. Control system 102 may further include a clock to determine elapsed time for various applications discussed herein.

Sensors 105 may also be included within the transponder 19 for determining physical or environmental characteristics within the container 30, such as the pressure, liquid level, and temperature. Positioning of the ball 26 within the container chamber 34 allows for the sensors to accurately determine characteristics related to the container 30 and/or its contents 28. Alternatively, the sensors 105 may be external to the ball 26, such as within the fill tube 22, or mounted on one of the walls. In this alternative embodiment, the transponder 19 receives signals from the sensors 105.

Some wireless communications devices 19, such as that described in U.S. Pat. No. 5,585,953, entitled "IR/RF radio transceiver and method," incorporated herein by reference in its entirety, have both transmit and receive capability and can be used in the present invention. Other wireless communication devices 19, such as a transponder 19, have receive capability and use the energy received to communicate back, such as described in U.S. Pat. No. 6,078,259 entitled "Radio frequency identification tag," incorporated herein by reference in its entirety.

FIG. 3 depicts how communication is achieved with the transponder 19. An interrogation reader 120 contains interrogation communication electronics 122 and an interrogation antenna 124. The interrogation reader 120 communicates to the transponder 19 by emitting an electronic signal or command 126 modulated in a frequency through the interrogation antenna 124. The interrogation antenna 124 may be any type of antenna that can radiate a modulated signal 126 through a field 128, so that a compatible device, such as the transponder 19, can receive such signal 126 through its own antenna 106. The field 128 could be any of a variety of different types used in electronic communications including electromagnetic, magnetic, or electric. The signal 126 is a message containing information and/or specific instructions for the transponder 19.

When the transponder antenna 106 is in the presence of the field 128 emitted by the interrogation reader antenna 124, the wireless communication electronics 104 are energized thereby energizing the transponder 19. The transponder 19 remains energized so long as its antenna 106 is in the field 128 of the interrogation reader 120. The wireless communication electronics 104 demodulates the signal 126 and sends the message containing information and/or specific instructions to the control system 102 for appropriate actions. For example, the request in the message may be for the transponder 19 to communicate information about the contents 28 housed within the container 30, including date of manufacture, place of manufacture, and type of product 28 within the container 30. The message may also be instructions to communicate information regarding the temperature of the container 30 and/or its contents 28, their pressure levels, etc. The transponder 19 communicates information to the interrogation reader 120 by altering the contents of the signal 126.

Alternative forms exist for communicating with a transponder 19, or other wireless communication device 19. For instance, the transponder 19 may have a transmitter that can send information to the interrogation reader 120 without having to use the signal 126 as the means for communication. The transponder 19 may have its own power source, such as a battery or an energy storage unit that is charged by energy when the transponder 19 is in the field 128 of the signal 126. It is understood to one of ordinary skill in the art there are many other manners in which to communicate with a wireless communication device 10 such as a transponder 19, and that the present invention is not limited to the particular manner described above. The wireless communication device 19 in the present invention can be any type of device that allows reception of wireless, electronic communications and is able to communicate in response thereto.

Transponder in Ball

In one embodiment, the ball 26 is constructed of a conductive material, such as metal or stainless steel. A stainless steel ball 26 is common in containers 30, because it will not contaminate food products stored in the container 30. A ball 26 constructed of a conductive material may be used if the antenna signal 126 is not obstructed, such that communication can be achieved between the interrogation reader 120 and the transponder 19. The conductive ball 26 forms at least a portion of the antenna 124 as the ball 26 functions to radiate the antenna's 106 energy for communication. Alternatively, the ball 26 may be constructed of a non-conductive material if the antenna signal 126 is obstructed during communication between the interrogation reader 120 and the transponder 19. In one embodiment, the ball 26 is constructed of a consumption safe plastic, such as polypropylene.

The ball 26 is preferably hollow and contains the transponder 19 within. The transponder 19 is secured within the ball 26 to prevent its movement against the ball's 26 inner edges, that could cause damage. Alternatively, the ball 26 is solid with the transponder 19 mounted within the middle. Preferably, the transponder 19 is centered within the ball 26 to minimize distortions in the transmitted and received signals 126. Because the ball 26 may rotate and change orientation relative to the container 30 during use, the transponder 19 and antenna 106 inside the ball 26 may also change orientation in the same manner. Therefore, the present invention may include an antenna 106 radiation pattern is relatively independent of the ball's 26 orientation.

Figure 4A:
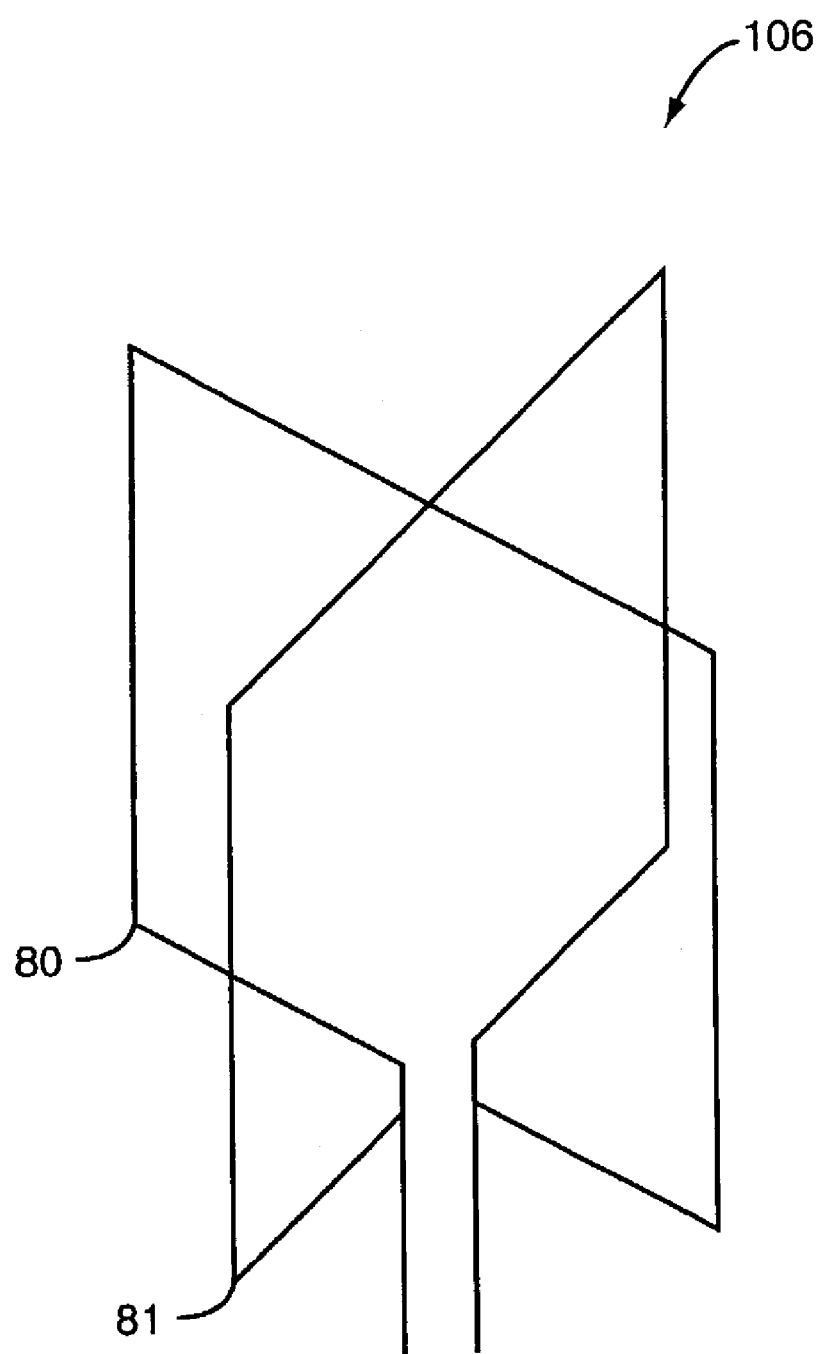
FIG. 4A is a schematic diagram of an orientation independent antenna arrangement.

FIG. 4A illustrates an embodiment for an antenna arrangement 106 that is relatively orientation independent. This antenna arrangement 106 is particularly useful for lower frequency communications in the MHz range or lower. For low frequency antennas, coupling varies with cos θ, giving a null at a relative 90-degree angle. The antenna 106 includes two coils 80, 81 mounted 90-degrees relative to each other tuned to the desired operating frequency. For low frequency operation, each coil 80, 81 exhibits a cos θ characteristic signal pattern giving a null at a relative 90-degree angle. The purpose of the antenna arrangement 106 illustrated in FIG. 4A is to provide an antenna 106 with a signal pattern that substantially eliminates this 90-degree null for a low frequency antenna 106. A resultant output is created from the sum of the squares of the signal patterns for each of the two coils 80, 81 is performed to eliminate any nulls. In this manner, there is always a signal generated from at least one coil 80 that is not null, thereby making the orientation angle of antenna 106 relatively independent with respect to communications.

Figure 4B:
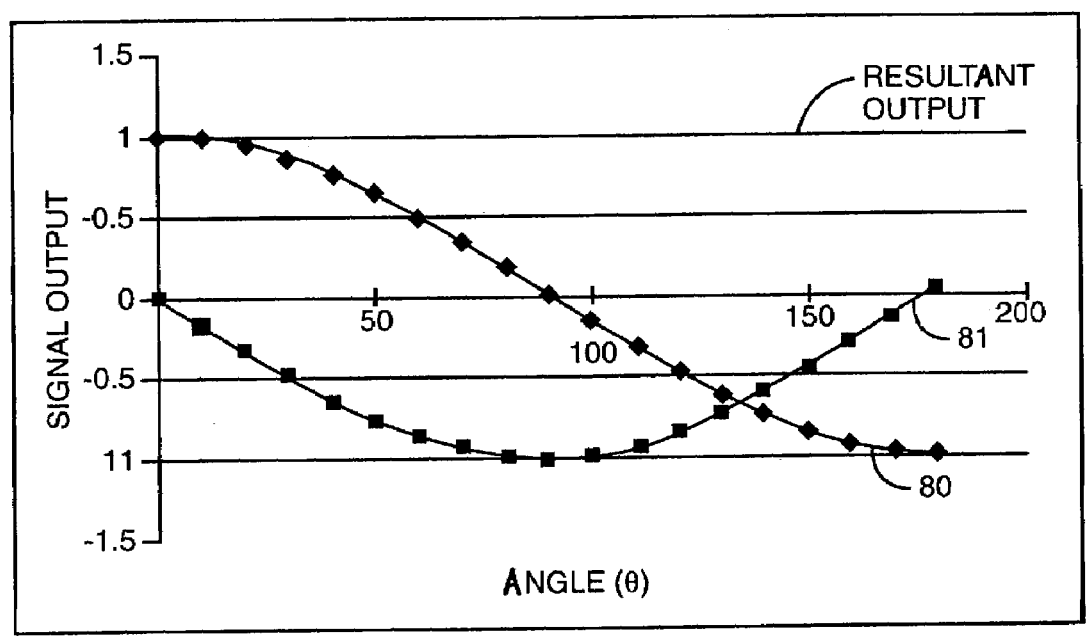
FIG. 4B is a schematic diagram of the coil signals from the antenna arrangement illustrated in FIG. 4A.

FIG. 4B illustrates the signal pattern outputs for each of the two coils 80, 81, and the resultant output. The resultant output is constant, representing orientation independence in one plane. This technique yields an effective signal received up by the antenna 106 pattern without nulls, thus making it independent of the relative angle of antenna 106 orientation. For short range of communication between the transponder 19 and the interrogation reader 120, the antenna 106 mounted in the ball 26 uses two solenoid coils 80, 81 to operate at either 125 kHz or 13.56 MHz. In another embodiment, the antenna arrangement 106 has three coils by further adding an additional orthogonal coil to the two coils 80, 81, representing an effectively isotropic power coupling and antenna arrangement. This provides an antenna arrangement 106 that is relatively orientation independent in more than one plane. The same principles, described above for a two-coil antenna arrangement, also apply for an antenna arrangement with three or more coils.

Temperature Sensing

Temperature sensing of the container 30, its contents 28, and/or the transponder 19 may be accomplished when the transponder 19 is located in the valve assembly 20, the ball 26, or the gasket 24 as described in the following techniques below.

Temperature Technique 1

Temperature sensing may be accomplished by placing a temperature sensor 105a in the valve assembly 20 and/or within the ball 26 or gasket 24. The temperature sensor 105a may be contained within the transponder 19, or external to the transponder 19. The temperature sensor 105a may be any variety of temperature sensing elements, such as a thermistor or chemical device. One such temperature sensor 105a is described in U.S. Pat. No. 5,959,524, entitled "Temperature sensor," incorporated herein by reference in its entirety. The temperature sensor 105a may also be incorporated into the transponder 19 or control system 102, like that described in U.S. Pat. No. 5,961,215, entitled "Temperature sensor integral with microprocessor and methods of using same," incorporated herein by reference in its entirety. However, the present invention is not limited to any particular type of temperature sensor 105a for this temperature technique.

The temperature sensor 105a is coupled to the control system 102. In this manner, the control system 102 can communicate the temperature to the wireless communication electronics 104, to in turn communicate the temperature of the container 30 and/or its contents 28 to an interrogation reader 120 when desired.

In an exemplary embodiment, the ball 26 is in thermal contact with the container contents 28. Placement of the sensor 105 within the ball provides for an accurate temperature measurement. Thermal contact is obtained either directly by placing the ball 26 in direct contact with the contents 28, or indirectly by placing the ball 26 is in thermal contact with the biasing member 29 and/or fill tube 22 that is in direct contact with the contents 28. As the container 30 moves through a facility during storage or processing, the temperature may be obtained through a combination of direct and indirect readings.

The temperature of the container 30 and/or its contents 28, as determined by the temperature sensor 105a, may be read by the transponder 19 when directed to do so by the interrogation reader 120. The transponder 19 may also be programmed to ascertain temperature through use of the temperature sensor 105a at times when the transponder 19 is not in the field 128 of the interrogation reader 120, such as during transit. The transponder 19 may also store the temperature readings in memory 108, to be communicated to the interrogation reader 120 at a later point in time.

Temperature Technique 2

Figure 5A:
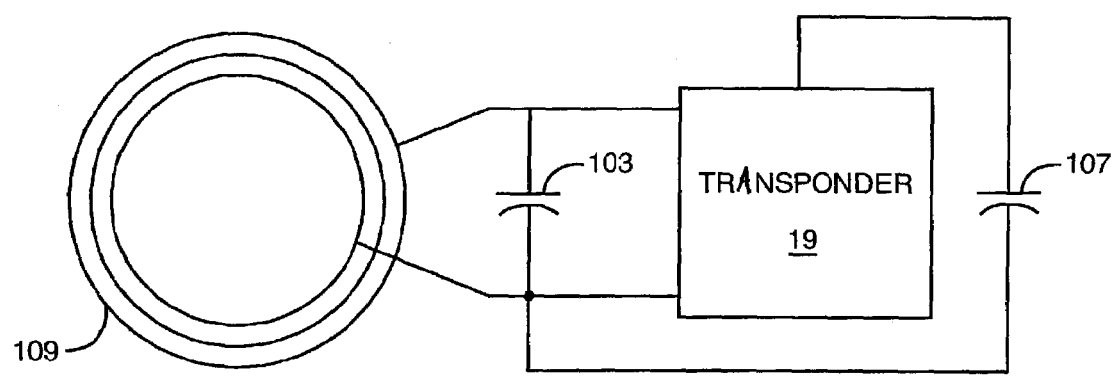
FIG. 5A is a schematic diagram of a transponder arrangement to determine temperature of the transponder using a discharge capacitor.

FIG. 5A illustrates another method for determining temperature of the transponder 19. The transponder 19 has a capacitor that discharges in relation to temperature during the transponder's 19 journey. By determining the temperature of the transponder 19, the temperature of the container 30 and/or its contents 28 may also be ascertained by correlating the discharge to the temperature. A capacitor 107, called a "discharge capacitor" 107 for convenience sake, is connected at one end to the same node as a tuning capacitor 103. The tuning capacitor 103 is connected in parallel to the antenna 109 and the transponder 19. The other end of the discharge capacitor 107 is connected to the transponder 19. The energy stored in the discharge capacitor 107 discharges over time, dependent upon on the temperature of the transponder 19 during its journey. It should be noted that the present invention should not be limited to the particular configuration of the discharge capacitor 107.

When the transponder 19 is in the presence of the interrogation reader field 128, the discharge capacitor 107 is charged. The transponder 19 determines the amount of charge applied to the discharge capacitor 107, and stores such in memory 108. As the container 30 moves away from the interrogation reader field 128, the transponder 19 internally keeps track of the elapsed time between the charging of the discharge capacitor 107 and the present time, using a clock. This transponder 19 may operate when outside of the field 128, by providing its own power source, such as a battery or capacitor that is charged when the transponder 19 in the field 128 of the interrogation reader 120. Use of a capacitor as a power source for a transponder 19 is described in provisional application No. 60/378,384 entitled "RFID temperature device and method," filed on May 7, 2002, assigned to the same assignee of the present invention, and incorporated herein by reference in its entirety. The discharge rate f the discharge capacitor 107 can be related to temperature in a linear manner. When the transponder 19 is interrogated by the interrogation reader 120 at a second point in time, the charge left on the discharge capacitor 107 is used to determine an average temperature during the journey.

An example of this technique is described below. For instance, the discharge rate of the discharge capacitor 107 at different temperatures may be as follows:

| Temperature (Celsius) | Discharge Rate |
|---|---|
| 10 degrees | 0.2 micro Amperes |
| 20 degrees | 0.4 micro Amperes |

Using the integrated discharge rates for the discharge capacitor 107, as shown above, the discharge capacitor 107 is 0.1 Farads and is charged to 1 Volt at time zero during the transponder's 19 first point of interrogation at an interrogation reader 120. Fifty hours later, the transponder is interrogated again by a second interrogation reader 120. At this time, the remaining charge on the discharge capacitor 107 is 0.064 Coloumbs.

Charge in Coloumbs (Q) is equal to the capacitance (C) in Farads times volts (V) as shown below:

$$Q = CV$$

Current (I) equals charge (Q) divided by time (t). Assuming a linear current to time ratio, current (I) is equal to the capacitance (C) times collective the initial voltage applied to the capacitor at time zero (Vzero) minus the measure voltage of the capacitor at a time in point later (Vt) divided by time (t) in seconds as shown below:

$$I = \frac{C(Vzero - Vt)}{t}$$

In the particular example above, capacitance C is 0.1 Farads. The initial voltage is 1 Volt. The voltage fifty hours later (Vt) is 0.64 Volts. Time (t) is fifty hours, which is 180,000 seconds. Applying the formula above, current (I) is measured at 0.2 micro Amperes which relates to a 10-degree temperature, based on the temperature characteristic of the discharge capacitor 107 used for this particular example. If the same discharge occurred over a period of twenty-five hours, the current (I) would be equal to 0.4 micro Amperes that relates to a 20-degree temperature based on the temperature characteristic of the discharge capacitor 107 used for this particular example.

Figure 5B:
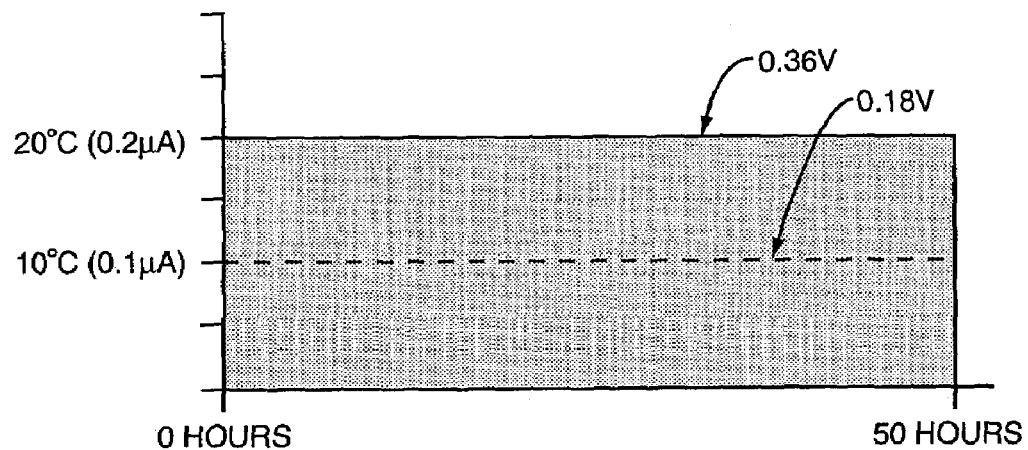
FIG. 5B is a schematic diagram of a discharge capacitor temperature technique for a constant temperature.
Figure 5C:
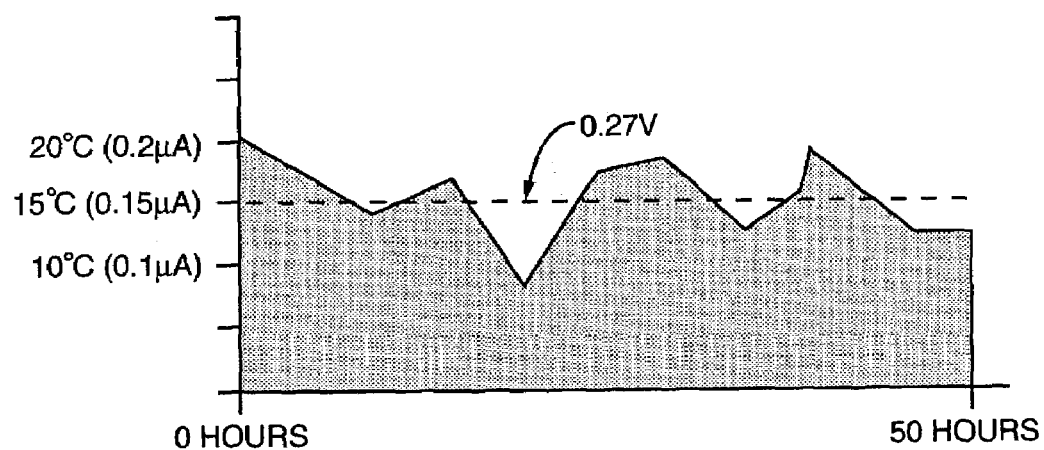
FIG. 5C is a schematic diagram of the discharge capacitor temperature technique for a variable temperature.

FIGS. 5B and 5C show the same discharge technique, described above, for determining temperature associated with the container 30 and/or its contents 28. Again, the particular capacitance of the discharge capacitor 107 is 0.1 Farads, the initial voltage is 1 Volt, and the discharge time is fifty hours or 180,000 seconds. FIGS. 5B and 5C show a graphical representation of discharge time versus temperature with the X-axis representing discharge time, and the Y-axis representing amperage and its corresponding temperature that is constant. The total charge (Q) taken from the discharge capacitor 107 is represented by the area under the graph, which is the same as its integration. In the present example illustrated in FIG. 5A, the discharge time is fifty hours, and the voltage measured at fifty hours is 0.36 Volts. Using the formula above, the current (I) for the integrated area equaling 0.2 micro Amperes equals 20-degrees Celcius. Similarly, FIG. 5B illustrates a fifty-hour discharge time with a 0.18 Volts reading at fifty hours, equaling a 0.1 micro Amperes equaling 10 degrees Celcius. If the remaining charge on the discharge capacitor 107 is above or below a predetermined amount, this may be an indication that the temperature of the transponder 19 may have been too high or too low, respectively, from desired temperature characteristics. Certain contents 28 may be sensitive to extreme temperatures that become either too high or too low at any time.

FIG. 5C is a graphical representation of a variable temperature during the container's 30 journey. In this example, the total current (I) or integrated area can be compared against a quality factor that is based on time. For example, if the acceptable quality is represented by a total area of less than 0.15 micro Amperes per hour over a fifty hour discharge, a comparison may be made to the actual integrated area to determine if the calculated current (I) is below the 0.15 micro Amperes per hour maximum rating to determine if the derived temperature is acceptable. Similarly, it may be desired that the temperature be deemed acceptable, if the area is not more or less than a percentage of an acceptable quality.

Other techniques for the transponder 19 to correlate discharge in a discharge capacitor 107 to temperature in a non-linear fashion are also applicable. A characteristic curve and formula may be provided to correlate the discharge of the discharge capacitor 107 into temperature of the transponder 19 for given characteristics of the transponder 19, its operation and the reservoir capacitor 103. Either the discharge or the values of the charge of the discharge capacitor 107, at first and second points, are compared to the characteristic curve to yield a temperature. Alternatively, a look-up table may be provided in the transponder 19 memory 108 that correlates total discharge of the discharge capacitor 107, or an amount of charge in the discharge capacitor 107 at first and second point in time, to a particular temperature.

With the aforementioned technique for temperature determination, the temperature sensing method is performed without devices external to the transponder 19, and is therefore particularly useful for an embodiment where the transponder 19 is mounted inside the ball 26.

Temperature Technique 3

Another technique for sensing the temperature is referred to herein as the "energy absorption technique." A temperature unstable antenna coil 106, connected the transponder 19, absorbs energy from the interrogation reader field 128 at different frequencies depending on the temperature of the transponder 19. There is a correlation between the operating frequency of the transponder 19 and the temperature of the transponder 19. The frequency at which the temperature unstable antenna coil 106 absorbs maximum energy from the field 128, referred to herein as the "maximum energy absorption frequency," may be correlated to the temperature of the transponder 19. The temperature of the container 30 and/or its contents 28 may be ascertained from the temperature of the transponder 19. This technique can be used to determine the temperature of the container 30 and/or its contents 28 at interrogation points when the transponder 19 is being interrogated by an interrogation reader 120. This technique does not apply to temperature determination while the container 30 is in transit between various interrogation points, since an interrogation reader 120, or other similar device, is required.

Absorption of energy at a certain frequency is related to the temperature at a particular operating frequency of a transponder 19. The transponder 19 operating frequency is defined below as:

$$\text{Frequency} = \frac{1}{2\pi(LC)^{1/2}}$$

L represents the inductance of the antenna coil 109, and C represents the capacitance of the tuning capacitor 103.

At initialization of the transponder 19, the interrogation reader 120 emits varying frequencies to determine maximum energy absorption frequency from the field 128 by the transponder 19. During the initialization, the current temperature is known by interrogation reader 120 through use of its own temperature sensor or other temperature sensing device. Once the maximum energy absorption frequency is determined, the interrogation reader 120 communicates the actual temperature being measured by the interrogation reader 120 and the maximum energy absorption frequency of the transponder 19 to the transponder 19 for storage in memory 108. The interrogation reader 120 determines the maximum energy absorption frequency from the field 128 by the transponder 19 in a number of ways, such as determining when there is a voltage drop at the antenna 124 of the interrogation reader 120. At a later point in time when the transponder 19 is within the interrogation reader field 128, the interrogation reader 120 again interrogates the transponder 19 to determine its new maximum energy absorption frequency. The interrogation reader 120 also retrieves the calibrated temperature and maximum absorption frequency previously stored within the transponder 19. A temperature is determined as a function of the difference between the first or calibrated maximum energy absorption frequency of the transponder 19 and the second maximum energy absorption frequency. The interrogation reader 120 perform this determination and correlates such to a corresponding temperature of the transponder 19 during its journey.

One way to accomplish this temperature technique is to provide a characteristic curve between different maximum energy absorption frequencies of the transponder 19 and temperatures into the interrogation readers 120 before operation. The interrogation reader 120 correlates the maximum energy absorption frequency of the transponder 19 to the temperature of the transponder 19 during its journey. Alternatively, a look-up table may be provided in the transponder 19 that correlates a maximum energy absorption frequency of the transponder 19 to a particular temperature of the transponder 19 during its journey.

There are other techniques that may be used to correlate the maximum energy absorption frequency to the temperature of the transponder 19, and therefore the temperature of the container 30 and/or its contents 28. The present invention is not limited to any one particular method.

Liquid Level

The amount of liquid 28 within the container 30 may be determined using the transponder 19 mounted inside the ball 26 and a liquid level sensor 105*b* located in the transponder 19 itself or associated with the transponder 19, such as the fill tube 22. As the liquid 28 varies, the resonance of the fill tube 22 varies. The transponder 19 mounted inside the ball 26 contains magnetic means to drive and sense the fill tube 22 resonance, thereby allowing the transponder to determine the level of the liquid in the container.

The present invention measures liquid 28 level by measuring the resonance response of the fill tube 22. It is known that a container 30 containing liquid 28 or other material will generate a specific increased resonance based on a particular emitted frequency based on the level of liquid 28 or liquidous material 28 contained in the container 30. This frequency at which the maximum resonance is generated and measured is known as the "resonance frequency," and is referred to herein as such.

A particular type of level sensor 105*b*, known as a level actuator 105*b*, may be associated with the transponder 19 to measure mechanical resonance associated with the fill tube 22. In an exemplary embodiment, the level actuator 105B global search is piezo-electric. The fill tube 22 is in contact with the contents 28 of the container 30. The level actuator 105*b* may be internal to the transponder 19 or associated with the transponder 19 externally. The level actuator 105B may be contained within the ball 26 in the embodiment in which the transponder 19 is contained within the ball 26. Also, the level actuator 105B may be contained in the gasket 24 in the embodiment in which the transponder 19 is contained in the gasket 24. The transponder 19 powers the level actuator 105B either when the transponder 19 is in the field of the interrogation reader 120 or if the transponder 19 has a power source. The level actuator 105B does not have to be contained in the ball 26 or the gasket 24 so long as it is associated with the transponder 19 to receive power and is associated with the fill tube 22 to emit and/or receive resonance signals from the fill tube 22 or the air surrounding the fill tube 22.

The level actuator 105B emits frequencies over a given range in the fill tube 22 itself, the air surrounding the fill tube 22, or a gaseous material inserted into the fill tube 22 to determine the resonance frequency that correlates to a particular liquid 28 level. One method of correlation is to provide within the transponder 19 a look-up table of different liquid levels for different resonance frequencies based on predetermined characteristics of the container 30. Another method is to provide the transponder 19 a formula that takes as input the resonance frequency and returns a liquid level based on the characteristics of the container 30. After the transponder 19 correlates the resonance frequency to a particular liquid 28 level, the liquid 28 level can be stored in memory 108 or communicated by the transponder 19 to the interrogation reader 120, or both when desired.

One level actuator 105B can be provided that sweeps the aforementioned frequency range. The voltage supplied to the level actuator 101 by the transponder 19 and/or its power source will substantially lessen when the resonance frequency is generated by the level actuator 101. Alternatively, two level actuators 101 can be provided whereby one level actuator 101 emits the frequency signals in the desired range, and the other level actuator 105B receives a signal in response representative of the resonance. The transponder 19 receives the receiving level actuator 105Bhttp://money-.cnn.com/2002/05/22/news/companies/abercrombie.ap/index.h tm signals and determines the resonance frequency.

It is should be understood that it is obvious to one of ordinary skill in the art to provide other methods of determine liquid level in a container 30 using resonance and that the present invention is not limited to any one particular method.

Antenna Arrangements

The present invention provides an antenna 106, and the present invention is not limited to a particular type of antenna arrangement 106. However, the following discussion discusses different types of antenna arrangements that may be employed to provide the antenna 106 component of the present invention.

FIG. 6 shows an antenna arrangement whereby the antenna 106 is contained within the packaging of the transponder 19. The transponder 19 is located in the gasket 24. The ball 26 is seated on the biasing member 29 and seats against the seated edges 27 for closing the opening 36. In this particular embodiment, the antenna 106 is contained within the transponder 19 packaging. No feed or coupling lines for the antenna 106 are connected external to the transponder 19. For high frequency communications, usually in the GHz range and above, the antenna 106 is short enough to be included into the transponder 19 packaging itself rather than external to the transponder 19.

Figure 7:
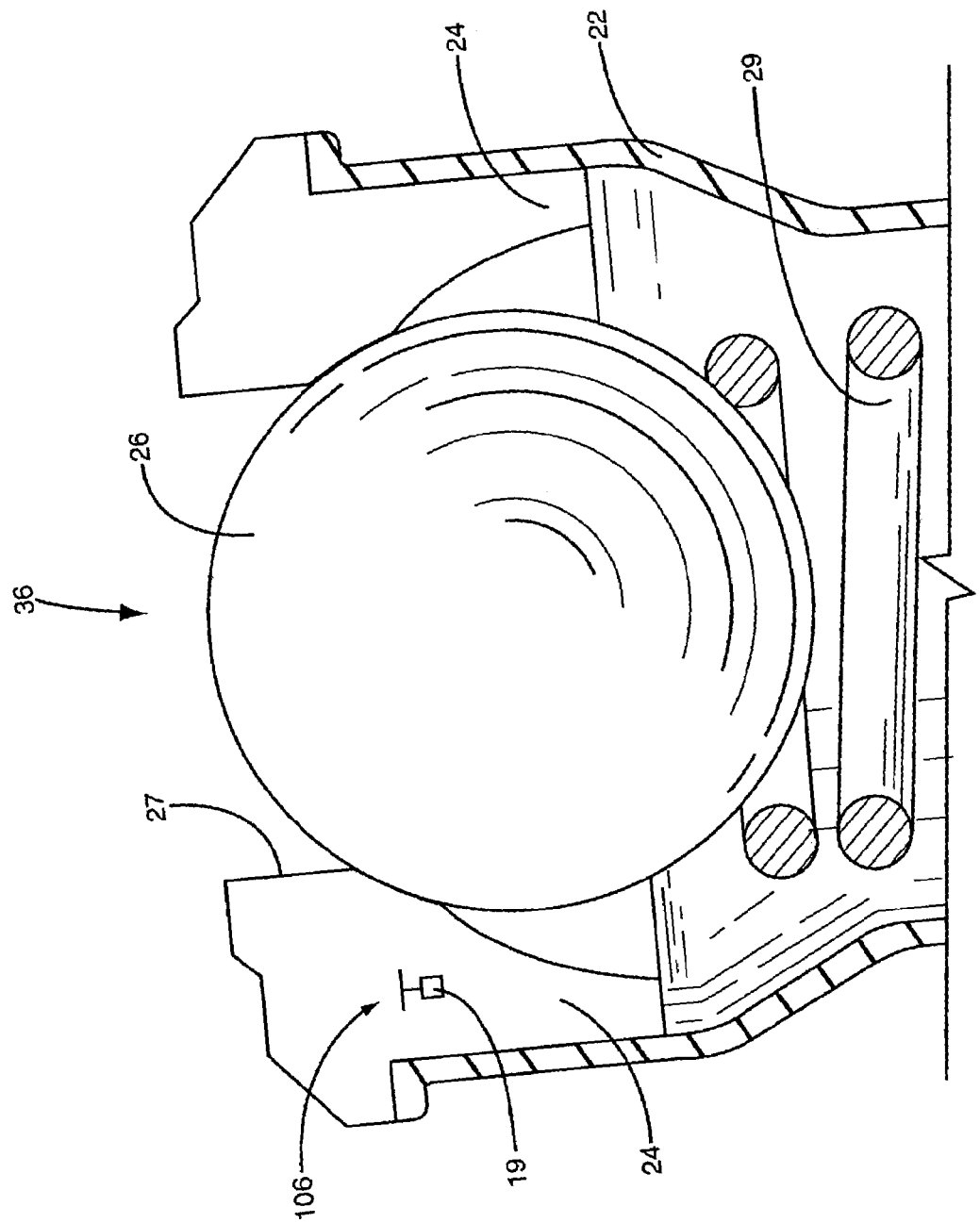
FIG. 7 is a schematic diagram of an antenna arrangement with the antenna external to the transponder packaging.

FIG. 7 shows an antenna arrangement whereby the antenna 106 is provided external to packaging of the transponder 19. A longer antenna 106 is usually required, than is usually practical to be included in the transponder 19 packaging, if the transponder 19 communicates at lower frequencies in the MHz range or below. The antenna 106 is provided in the gasket 24 and is connected to the transponder 19. Since the gasket 24 is non-conductive, placement of the antenna 106 will not in and of itself interfere with transponder 19 communication. However, there may be interference by other conductive parts of the container 30 that could affect communication of the transponder 19.

Figure 8:
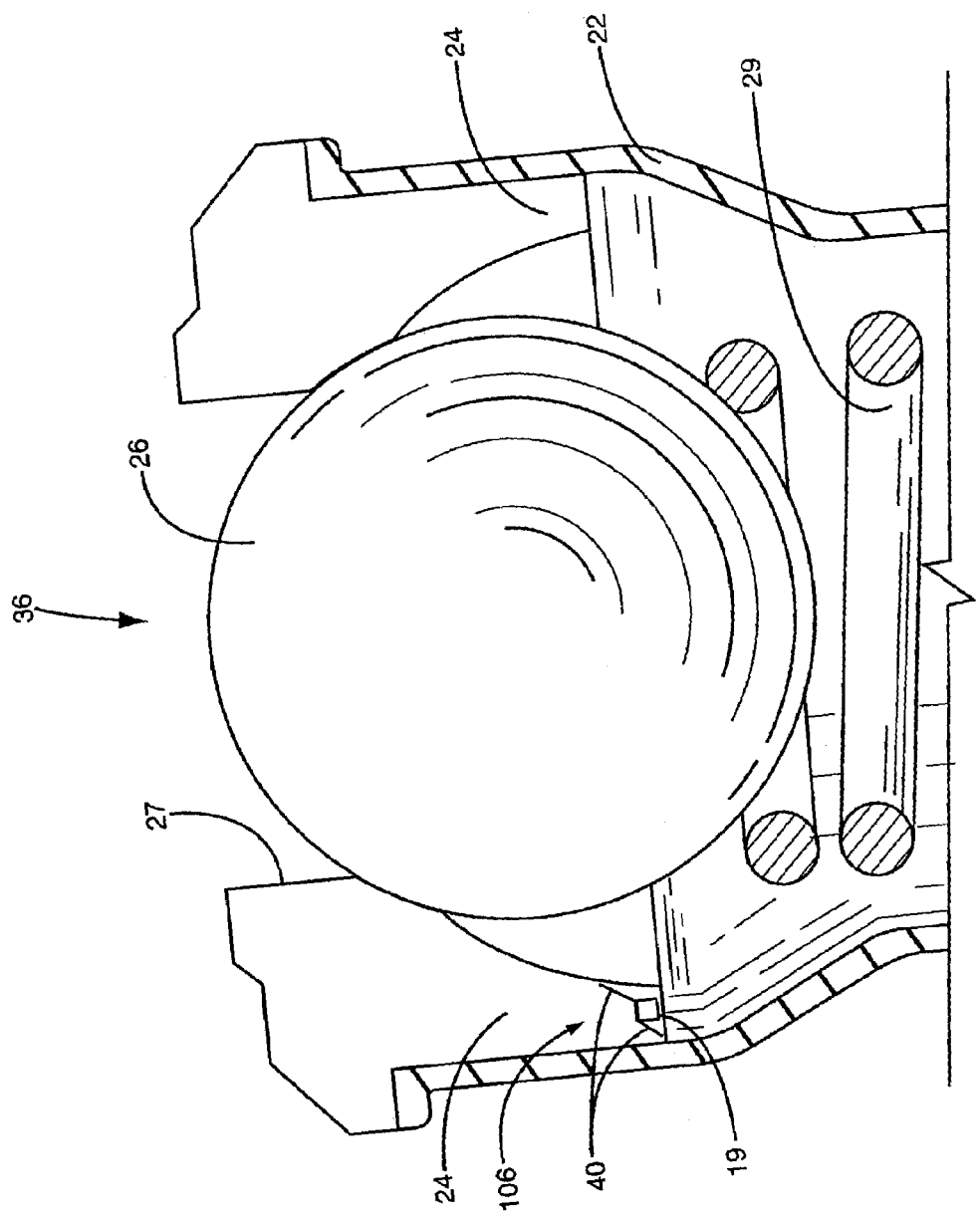
FIG. 8 is a schematic diagram of an antenna arrangement using couple connection.

FIG. 8 shows an antenna arrangement whereby the transponder 19 is provided in the gasket 24. Feed lines 40 are connected external to the transponder 19 and are not directly connected to a conductive surface. Instead, the feed lines 40 are reactively coupled with the edge of the gasket 24 in close proximity to the ball 26 and the fill tube 22. The feed lines 40 reactively couple with the conductive surface of fill tube 22 and ball 26 to provide an antenna 106 suitable for communications.

Figure 9:
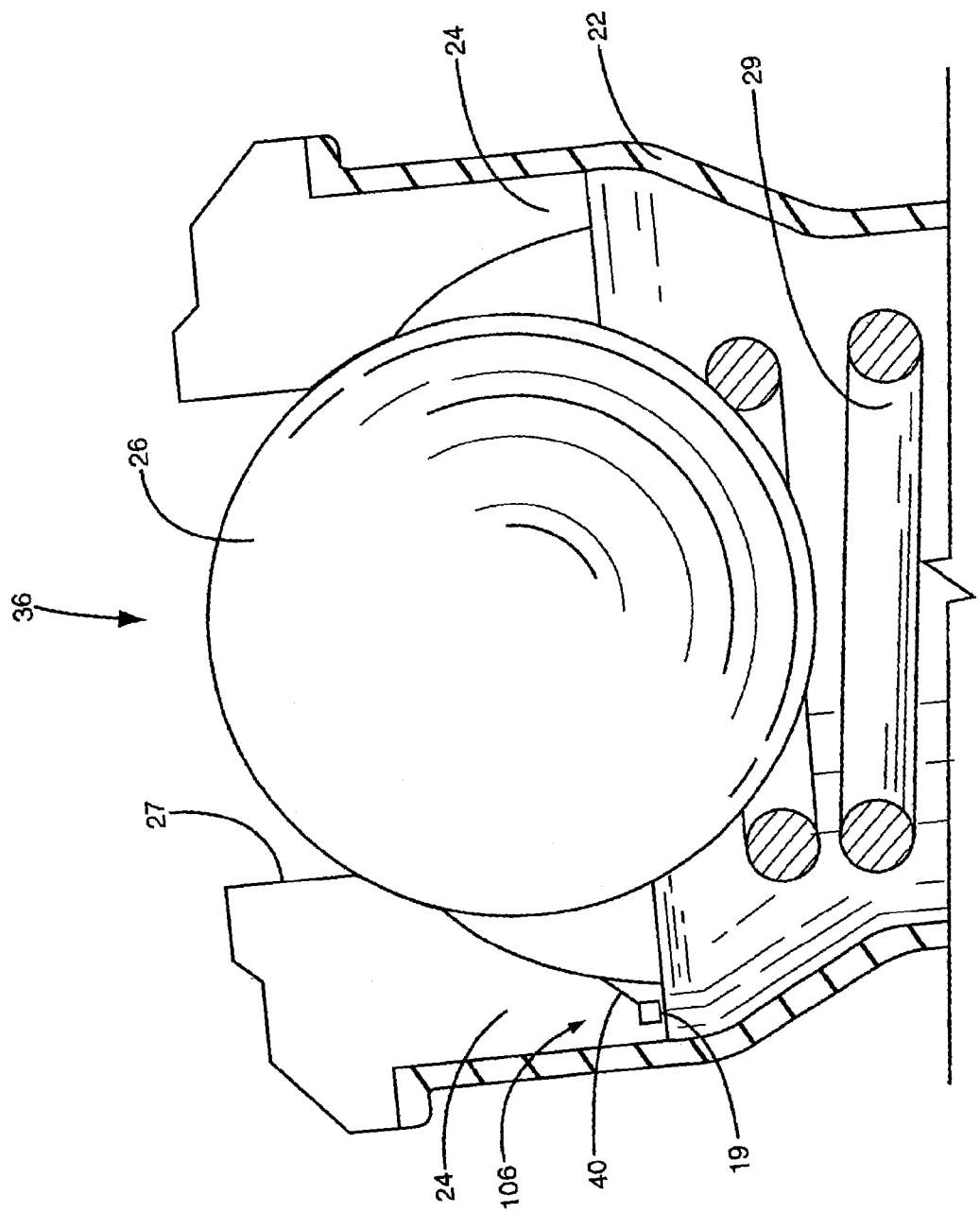
FIG. 9 is a schematic diagram of a slot antenna arrangement using a directly connected feed line.
Figure 10:
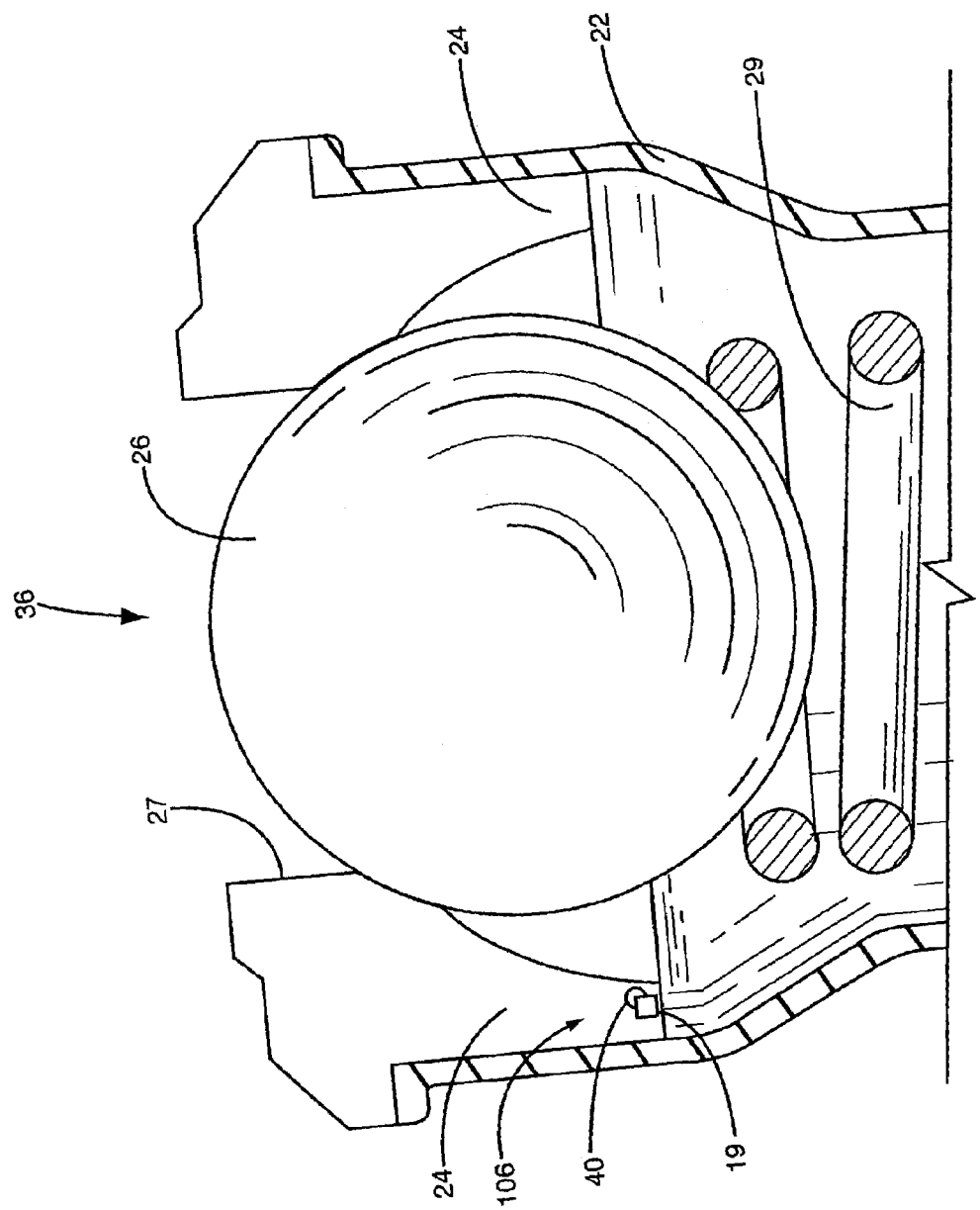
FIG. 10 is a schematic diagram of a slot antenna arrangement using a couple connected feed line.
Figure 11:
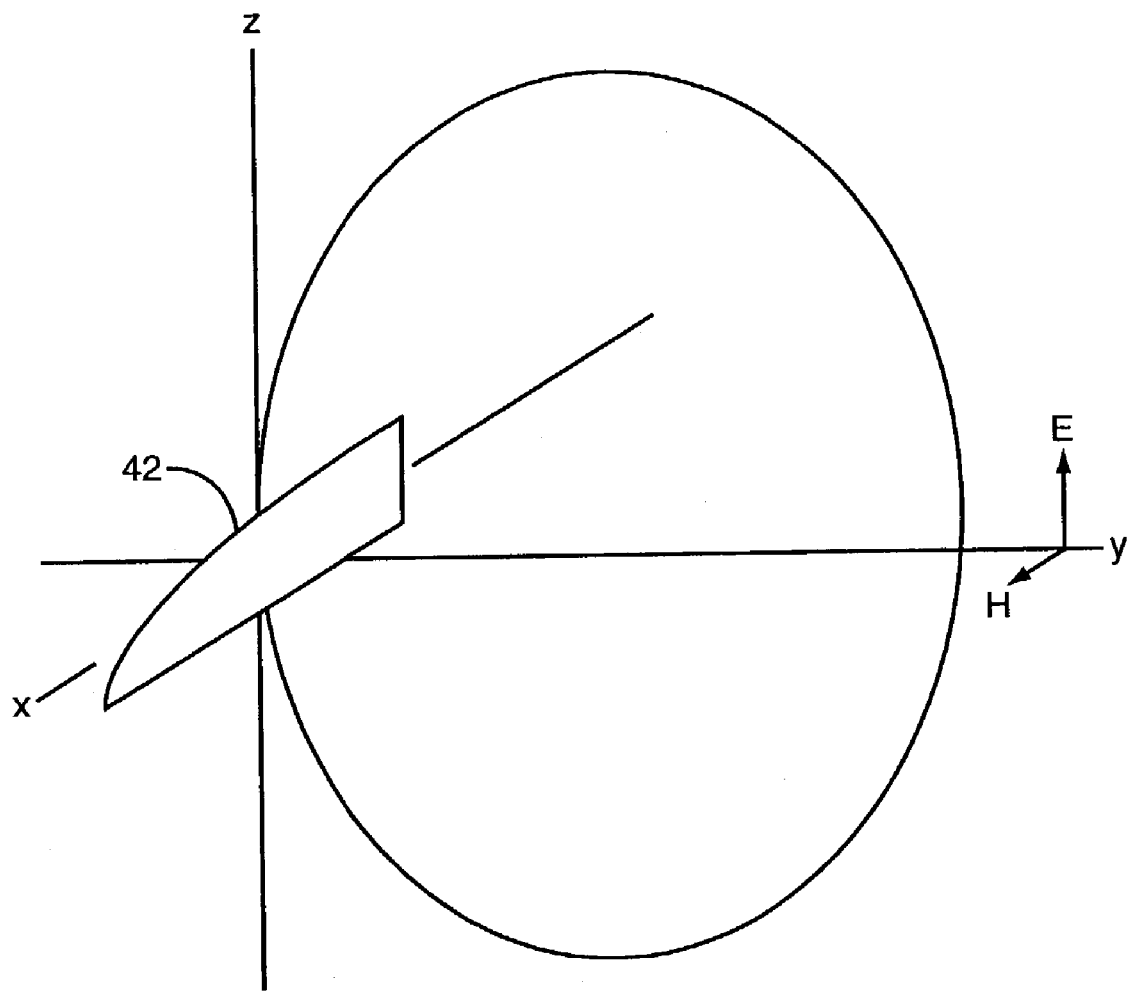
FIG. 11 is a schematic diagram illustrating the radiation pattern of a typical slot antenna arrangement.

FIGS. 9 and 10 illustrate various configurations of a slot antenna arrangement. It is possible to provide an antenna 106 for the transponder 19 by using a slot 42 proximate to the gasket 24. A voltage signals provided by the transponder 19 through the feed lines 40 are fed to opposites sides of the slot 42. When the voltage signals are applied across the slot 42. The slot 42 radiates electromagnetic waves to form a slot antenna 106. The radiation pattern of a slot antenna 106 has the same shape as a traditional antenna arrangement, such as a dipole antenna, but the E and H fields are interchanged as illustrated in FIG. 11. More information about slot antennas and their operation are disclosed in U.S. Pat. No. 6,023,244, entitled "Microstrip antenna having a metal frame for control of an antenna lobe," and U.S. Pat. No. 4,975,711, entitled "Slot antenna device for portable radiophone," both of which are incorporated herein by reference in their entirety. It should be understood though that the exact radiation pattern may vary depending on the frequency of the transponder 19 and type of container 30 and may not be exactly like that of FIG. 11.

FIG. 9 illustrates one type of slot antenna arrangement whereby the transponder 19 is contained in the gasket 24. The feed line 40 is connected to the edge of the gasket 24 to a slot 42, formed between the edge of the gasket 24 and the ball 26. The slot 42 has a boundary where the ball 26 rests on the gasket 24 when biased upward by the biasing member 29. The slot also has a boundary formed by the edge of the gasket 24 and on the edge between the gasket 24 and the ball 26.

FIG. 10 illustrates an alternative type of slot antenna arrangement, whereby the feed lines 40 from the transponder 19 are not connected directly to the slot 42. Instead, the feed lines 40 are placed such that they are reactively coupled with the slot 42. Depending on the type of container 30 and valve assembly 20, it may be more advantageous to not connect the feed lines 40 directly to the slot 42, since the valve assembly 20 may move in different orientations and the feed line 40 connections may not be optimal during to this movement.

The voltage signal is applied to the feed lines 40 by the transponder 19 in a manner similar to a transformer. Similarly, when the slot 42 is exposed to electromagnetic radiation, a voltage signal appears across the coupling with the slot 42 and provides a good impedance-matching characteristic. This type antenna 106 may be simpler and less expensive to manufacture than a direct connection of feed lines 40 shown in FIG. 10.

Tracking

Figure 12:
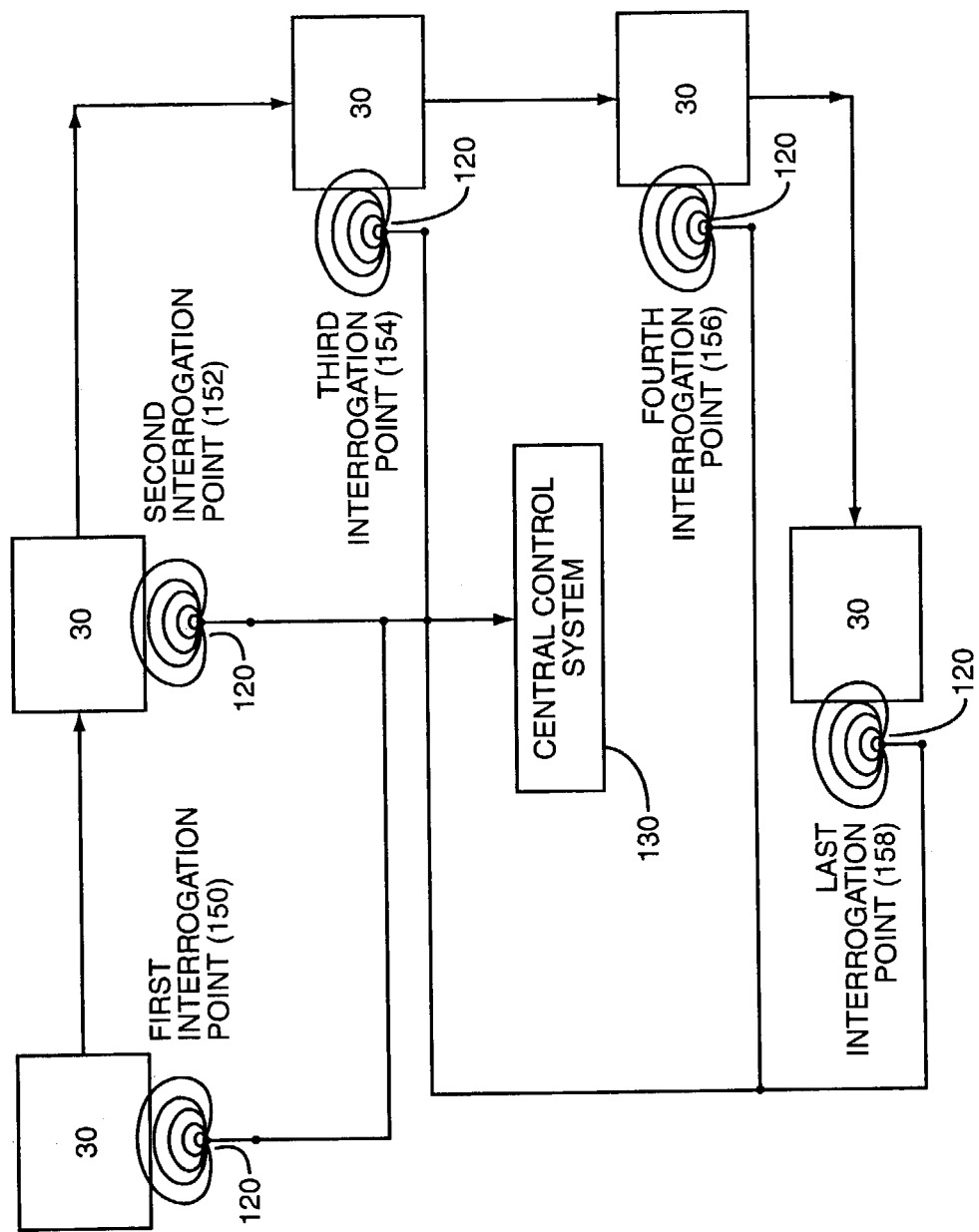
FIG. 12 is a schematic diagram illustrating a tracking and information system.

FIG. 12 illustrates a tracking system in which containers 30 containing transponders 19 can be tracked through an environment such as factory or distribution facility. For example, the transponder 19 connected to container 30 could pass a first interrogation point 150 that includes an interrogation reader 120. When the container 30 and its transponder 19 are in the presence of the interrogation reader 120 as described previously, a message containing information and/or a specific request for information may be transmitted by the interrogation reader 120 and received by the transponder 19. This process continues as the container 30 moves to a second interrogation point 152, a third interrogation point 154, a fourth interrogation point 156, and on to a last interrogation point 158.

A central control system 130 maintains the information from the interrogation readers 120 and monitors the movement of the containers 30 through the facility. The information received by each of the interrogation readers 120 may be forwarded to the central control system 130 either through direct wiring or a network, such as a local area network (LAN) or wide area network (WAN). The central control system 130 could also send information to the interrogation reader 120 to be transmitted to the transponder 19 for identification purposes. The central control system 130 tracks the expected location of the containers 30 and may be alerted if it expects to receive information about a particular container 30 and does not.

During commissioning of each container 30, it may be necessary to place the container 30 containing the transponder 19 in range of an interrogation reader 120 in order to erase previously stored information in memory 108 or to store particular data or configuration information about the container 30 in memory 108, for later use.

In the foregoing description, like-reference characters designate like or corresponding parts throughout the several views. Also, it is to be understood that such terms as "forward," "rearward," "left," "right," "upwardly," "downwardly," and the like are words of convenience that are not to be construed as limiting terms. Certain modifications and improvements will occur to those skilled in the art upon a reading of the foregoing description. One of ordinary skill in the art will recognize that there are different manners in which these elements can provide to accomplish the present invention.

It should also be understood that all such modifications and improvements have been deleted herein for the sake of conciseness and readability, but are properly within the scope of the following claims. The present invention is intended to cover what is claimed and any equivalents. The specific embodiments used herein are to aid in the understanding of the present invention, and should not be used to limit the scope of the invention in a manner narrower than the claims and their equivalents.

What is claimed is:

1. A device identifying a container containing contents, comprising:
    a valve assembly for controlling passage of the contents to and from the container, said valve assembly including a ball and positioned to be in contact with the contents inside the container; and
    a wireless communication device positioned with said valve assembly for wirelessly communicating information associated with the container, wherein said wireless communication device is mounted within said ball.

2. The device of claim 1, further including a temperature sensor operatively connected to said wireless communication device for determining the temperature associated with the container.

3. The device of claim 2, wherein said wireless communication device determines the temperature due to said temperature sensor being in thermal contact with the container.

4. The device of claim 2, wherein said wireless communication device includes a discharge capacitor associated with said wireless communication device.

5. The device of claim 4, wherein said wireless communication device linearly correlates a charge remaining on said discharge capacitor to the temperature.

6. The device of claim 4, wherein said wireless communication device includes a look-up table to correlate a charge remaining on said discharge capacitor to the temperature.

7. The device of claim 4, wherein said wireless communication device communicates the temperature to a control system if the charge remaining on said discharge capacitor exceeds a predetermined value.

8. The device of claim 4, wherein said wireless communication device further includes a means for communicating said temperature to a control system.

9. The device of claim 1, further including a liquid level sensor operatively connected with said wireless communication device for determining a liquid level within the container.

10. The device of claim 9, wherein said liquid level sensor includes an actuator to emit a frequency range whereby said wireless communication device determines a resonance frequency.

11. The device of claim 10, wherein said wireless communication device includes a memory having a characteristic curve for correlating said resonance frequency to a particular liquid level.

12. The device of claim 10, wherein said wireless communication device includes a memory having a look-up table for determining the liquid level.

13. The device of claim 10, wherein said actuator is piezo-electric.

14. The device of claim 9, wherein said liquid level sensor includes a transmit actuator and a receive actuator; and wherein said transmit actuator emits a frequency range and said receive actuator receives resonance responses to determine a resonance frequency.

15. The device of claim 14, wherein said transmit actuator and said receive actuator are both piezo-electric.

16. The device of claim 1, wherein the said wireless communication device further comprises an orientation independent antenna for receiving signals.

17. The device of claim 16, wherein said antenna further comprises a plurality of coils mounted at relative angles to each other.

18. The device of claim 17, wherein said plurality of coils each include a rectifier to square the signal from each said plurality of coils.

19. The device of claim 17, wherein each of said plurality of coils is arranged 90-degrees relative to each other.

20. The device of claim 1, wherein said ball is constructed of a conductive material.

21. The device of claim 1 wherein said ball is constructed of a food safe material.

22. The device of claim 1, further comprising an antenna associated with said wireless communication device.

23. The device of claim 22, wherein said antenna is internally positioned within said wireless communication device.

24. The device of claim 22, wherein said antenna is positioned at least partially external to said wireless communication device.

25. The device of claim 22, wherein said ball is constructed of a conductive material and said antenna is connected to and uses said ball as a radiator.

26. The device of claim 22, wherein said ball is constructed of a conductive material and said antenna is reactively coupled to and uses said ball as a radiator.

27. A device identifying a container containing contents, comprising:
    a valve assembly for controlling passage of the contents to and from the container, said valve assembly including a gasket and positioned to be in contact with the contents inside the container;

a wireless communication device positioned with said valve assembly for wirelessly communicating information associated with the container, wherein said wireless communication device is mounted within said gasket; and a temperature sensor operatively connected to said wireless communication device for determining the temperature of the contents inside the container.

28. The device of claim 27, wherein said wireless communication device determines the temperature due to said temperature sensor being in thermal contact with the container.

29. The device of claim 28, wherein said wireless communication device includes a discharge capacitor associated with said wireless communication device.

30. The device of claim 29, wherein said wireless communication device linearly correlates a charge remaining on said discharge capacitor to the temperature.

31. The device of claim 29, wherein said wireless communication device includes a look-up table to correlate a charge remaining on said discharge capacitor to the temperature.

32. The device of claim 29, wherein said wireless communication device communicates the temperature to a control system if the charge remaining on said discharge capacitor exceeds a predetermined value.

33. The device of claim 29, wherein said wireless communication device further includes a means for communicating said temperature to a control system.

34. A device identifying a container containing contents, comprising:

a valve assembly for controlling passage of the contents to and from the container, said valve assembly including a gasket and positioned to be in contact with the contents inside the container;

a wireless communication device positioned with said valve assembly for wirelessly communicating information associated with the container, wherein said wireless communication device is mounted within said gasket; and a liquid level sensor operatively connected with said wireless communication device for determining liquid level within the container.

35. The device of claim 34, wherein said liquid level sensor includes an actuator to emit a frequency range whereby said wireless communication device determines a resonance frequency.

36. The device of claim 35, wherein said wireless communication device includes a memory having a look-up table for determining the liquid level.

37. The device of claim 35, wherein said identification includes a memory having a characteristic curve for correlating said resonance frequency to a particular liquid level.

38. The device of claim 35, wherein said actuator is piezo-electric.

39. The device of claim 34, wherein said liquid level sensor includes a transmit actuator and a receive actuator; and wherein said transmit actuator emits a frequency range and said receive actuator receives resonance responses to determine a resonance frequency.

40. The device of claim 39, wherein said transmit actuator and said receive actuator are both piezo-electric.

41. An identification system, comprising:

a container having an outer wall forming an enclosed interior chamber for containing contents, said container further having an opening;

a valve assembly positioned over said opening for controlling the escape of said contents, wherein said valve assembly includes a ball positioned in said opening; and a wireless communication device mounted within said valve assembly to wirelessly communicate information associated with said container, wherein said wireless communication device is mounted within said ball.

42. The system of claim 41, wherein said container includes a fill tube extending between said opening and an interior portion of said container, said ball being in contact with said fill tube.

43. The system of claim 42, further including a biasing member positioned between and in contact with each of said ball and said fill tube.

44. The system of claim 41, further including a liquid level sensor operatively connected with said wireless communication device for determining liquid level within said container.

45. The system of claim 44, wherein said liquid level sensor includes an actuator to emit a frequency range whereby said wireless communication device determines a resonance frequency.

46. The system of claim 45, wherein said wireless communication device includes a memory having a characteristic curve for correlating said resonance frequency to a particular liquid level.

47. The system of claim 45, wherein said wireless communication device includes a memory having a look-up table for determining the liquid level.

48. The system of claim 45, wherein said actuator is piezo-electric.

49. The system of claim 44, wherein said liquid level sensor includes a transmit actuator and a receive actuator, wherein said transmit actuator emits a frequency range and said receive actuator receives resonance responses to determine a resonance frequency.

50. The system of claim 49, wherein said transmit actuator and said receive actuator are both piezo-electric.

51. An identification system, comprising:

a container having an outer wall forming an enclosed interior chamber for containing contents, said container further having an opening;

a valve assembly positioned over said opening for controlling the escape of said contents;

a wireless communication device mounted within said valve assembly to wirelessly communicate information associated with said container; and a temperature sensor operatively connected to said wireless communication device for determining the temperature of the contents inside said container.

52. The system of claim 51, further including a discharge capacitor associated with said wireless communication device.

53. The system of claim 52, wherein said wireless communication device includes a look-up table to correlate a charge remaining on said discharge capacitor to the temperature.

54. The system of claim 52, wherein said wireless communication device includes a characteristic curve to correlate a charge remaining on said discharge capacitor to the temperature.

55. The system of claim 52, wherein said wireless communication device communicates the temperature to a control system when the charge remaining on said discharge capacitor exceeds a predetermined valve.

56. An identification system, comprising;
a container having an outer wall forming an enclosed interior chamber for containing contents, said container further having an opening;
a valve assembly positioned over said opening for controlling the escape of said contents;
a wireless communication device mounted within said valve assembly to wirelessly communicate information associated with said container; and
an interrogation reader to interrogate said wireless communication device and further adapted to determine the temperature of said wireless communication device by determining a maximum energy absorption frequency of said wireless communication device.

57. The system of claim 56, wherein said interrogation reader correlates said maximum energy absorption frequency to a temperature using a look-up table.

58. The system of claim 56, wherein said interrogation reader correlates said maximum energy absorption frequency to said temperature using a characteristic curve.

59. An identification system, comprising:
a container having an outer wall forming an enclosed interior chamber for containing contents, said container further having an opening;
a valve assembly positioned over said opening for controlling the escape of said contents, said valve assembly including a gasket;
a wireless communication device mounted within said gasket to wirelessly communicate information associated with said container; and
a temperature sensor operatively connected to said wireless communication device for determining the temperature of the contents inside said container.

60. The system of claim 59, wherein said wireless communication device determines the temperature due to said temperature sensor being in thermal contact with said container.

61. The system of claim 59, wherein said wireless communication device includes a discharge capacitor associated with said wireless communication device.

62. The system of claim 61, wherein said wireless communication device linearly correlates a charge remaining on said discharge capacitor to the temperature.

63. The system of claim 61, wherein said wireless communication device includes a look-up table to correlate a charge remaining on said discharge capacitor to the temperature.

64. The device of claim 61, wherein said wireless communication device communicates the temperature to a control system if the charge remaining on said discharge capacitor exceeds a predetermined value.

65. The device of claim 61, wherein said wireless communication device further includes a means for communicating said temperature to a control system.

66. An identification system, comprising:
a container having an outer wall forming an enclosed interior chamber for containing contents, said container further having an opening;
a valve assembly positioned over said opening for controlling the escape of said contents, said valve assembly including a gasket;
a wireless communication device mounted within said gasket to wirelessly communicate information associated with said container; and
an interrogation reader to interrogate said wireless communication device and further adapted to determine the temperature of said wireless communication device by determining a maximum energy absorption frequency of said wireless communication device.

67. The system of claim 66, wherein said interrogation reader correlates said maximum energy absorption frequency to a temperature using a look-up table.

68. The system of claim 66, wherein said interrogation reader correlates said maximum energy absorption frequency to said temperature using a characteristic curve.

69. An identification system, comprising:
a container having an outer wall forming an enclosed interior chamber for containing contents, said container further having an opening;
a valve assembly positioned over said opening for controlling the escape of said contents, said valve assembly including a gasket;
a wireless communication device mounted within said gasket to wirelessly communicate information associated with said container; and
a liquid level sensor operatively connected with said wireless communication device for determining liquid level within said container.

70. The system of claim 69, wherein said liquid level sensor includes an actuator to emit a frequency range whereby said wireless communication device determines a resonance frequency.

71. The system of claim 70, wherein said wireless communication device includes a memory having a look-up table for determining the liquid level curve.

72. The system of claim 70, wherein said identification includes a memory having a characteristic curve for correlating said resonance frequency to a particular liquid level.

73. The system of claim 70, wherein said actuator is piezo-electric.

74. The system of claim 69, wherein said liquid level sensor includes a transmit actuator and a receive actuator, wherein said transmit actuator emits a frequency range and said receive actuator receives resonance responses to determine a resonance frequency.

75. The system of claim 74, wherein said transmit actuator and said receive actuator are both piezo-electric.

76. A method of monitoring information associated with contents contained within a container, comprising the steps of:
associating a wireless communication device within a valve assembly of the container wherein said valve assembly is positioned in contact with the contents;
determining information relating to a temperature associated with the contents; and
communicating information associated with said contents to an interrogation reader.

77. The method of claim 76, further including determining the temperature by determining the discharge in a discharge capacitor associated with said wireless communication device.

78. The method of claim 77, further including charging said discharge capacitor at a first time instant and determining the remaining charge of said discharge capacitor at a second time instant to determine the temperature based on a remaining charge of said discharge capacitor.

79. The method of claim 78, further including correlating said remaining charge with the temperature by using a look-up table.

80. The method of claim 78, further including correlating said remaining charge with the temperature using a characteristic curve.

81. The method of claim 77, further including communicating the temperature to a control system when said remaining charge exceeds a predetermined value.

82. The method of claim 77, further including communicating the temperature to said interrogation reader.

83. The method of claim 76, further including determining information relating to a liquid level by emitting a frequency range to determine a resonance frequency associated with the container.

84. The method of claim 83, further including correlating said resonance frequency to a particular liquid level using a characteristic curve stored in said wireless communication device.

85. The method of claim 83, further including looking up the temperature for said resonance frequency using a look-up table.

86. A method of monitoring information associated with contents contained within a container, comprising the steps of:
associating a wireless communication device within a valve assembly of the container wherein said valve assembly is positioned in contact with the contents;
determining a temperature of the contents by determining a maximum energy absorption frequency of said wireless communication device; and
communicating information associated with said contents to an interrogation reader.

87. The method of claim 86, further including correlating said maximum energy absorption frequency to a temperature using a look-up table.

88. The method of claim 86, further including correlating said maximum energy absorption frequency to said temperature using a characteristic curve.

* * * * *

UNITED STATES PATENT AND TRADEMARK OFFICE
CERTIFICATE OF CORRECTION

PATENT NO. : 7,224,273 B2
APPLICATION NO. : 10/422634
DATED : May 29, 2007
INVENTOR(S) : I.J. Forster It is certified that error appears in the above-identified patent and that said Letters Patent is hereby corrected as shown below:

| COLUMN | LINE | |
|---|---|---|
| 5 | 7 | "31" should read --31,-- |
| 6 | 29 | "such as described" should read --such as that described-- |
| 7 | 45 | "pattern is" should read --pattern that is-- |
| 7 | 59 | "output is" should read --output-- |
| 8 | 52 | "ball 26 is" should read --ball 26-- |
| 9 | 15 | "upon on" should read --upon-- |
| 9 | 30 | "in the field 28" should read --is in the field 28-- |
| 9 | 36 | "rate f" should read --rate of-- |
| 11 | 57 | "coil 109," should read --coil 106,-- |
| 12 | 8 | "perform" should read --performs-- |
| 12 | 47 | "105$b$," should read --105B,-- |
| 12 | 48 | "105$b$," should read --105B,-- |
| 12 | 52 | "105$b$" should read --105B-- |
| 13 | 28 | "It is should" should read --It should-- |
| 13 | 30 | "mine" should read --mining-- |
| 14 | 10 | "A voltage" should read --Voltage-- |
| 14 | 11 | "opposites" should read --opposite-- |
| 14 | 13 | "42. The" should read --42, the-- |
| 14 | 18 | "operation are" should read --operation is-- |

UNITED STATES PATENT AND TRADEMARK OFFICE
CERTIFICATE OF CORRECTION

PATENT NO. : 7,224,273 B2
APPLICATION NO. : 10/422634
DATED : May 29, 2007
INVENTOR(S) : I.J. Forster It is certified that error appears in the above-identified patent and that said Letters Patent is hereby corrected as shown below:

| COLUMN | LINE | |
|---|---|---|
| 14 | 26 | "that of" should read --that shown in-- |
| 14 | 44 | "during to" should read --during-- |
| 16 (Claim 21, line 1) | 48 | "claim 1" should read --claim 1,-- |

Signed and Sealed this

Fourth Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,224,273 B2  Page 1 of 1
APPLICATION NO. : 10/422634
DATED : May 29, 2007
INVENTOR(S) : I. J. Forster It is certified that error appears in the above-identified patent and that said Letters Patent is hereby corrected as shown below:

| COLUMN | LINE | ERROR |
|---|---|---|
| 19 (Claim 64, | 54 line 1) | "The device of claim 61," should read --The system of Claim 61,-- |
| 19 (Claim 65, | 58 line 1) | "The device of claim 61, should read --The system of Claim 61,-- |

Signed and Sealed this

Second Day of June, 2009

JOHN DOLL
*Acting Director of the United States Patent and Trademark Office*